US011938072B2

United States Patent
Sauser et al.

(10) Patent No.: US 11,938,072 B2
(45) Date of Patent: Mar. 26, 2024

(54) PATIENT SUPPORT APPARATUS HAVING A RADAR SYSTEM

(71) Applicant: Hill-Rom Services, Inc., Batesville, IN (US)

(72) Inventors: Frank E. Sauser, Cincinnati, OH (US); Steven D. Baker, Beaverton, OR (US)

(73) Assignee: Hill-Rom Services, Inc., Batesville, IN (US)

( * ) Notice: Subject to any disclaimer, the term of this patent is extended or adjusted under 35 U.S.C. 154(b) by 51 days.

(21) Appl. No.: 17/578,713

(22) Filed: Jan. 19, 2022

(65) Prior Publication Data
US 2022/0133562 A1    May 5, 2022

Related U.S. Application Data

(63) Continuation of application No. 17/032,275, filed on Sep. 25, 2020, now Pat. No. 11,253,411, which is a
(Continued)

(51) Int. Cl.
*A61G 7/00* (2006.01)
*A47C 27/08* (2006.01)
(Continued)

(52) U.S. Cl.
CPC ........ *A61G 7/05769* (2013.01); *A47C 27/083* (2013.01); *A61B 5/0507* (2013.01);
(Continued)

(58) Field of Classification Search
CPC ........ A61G 7/00; A61G 7/05; A61G 7/05769; A61G 2203/20; A61G 2203/34;
(Continued)

(56) References Cited

U.S. PATENT DOCUMENTS 5,560,374 A     10/1996  Viard
5,573,012 A  *  11/1996  McEwan ............ A61B 5/0809
                                                   600/595
(Continued)

FOREIGN PATENT DOCUMENTS

JP    2000-118338    4/2000
JP    2006-226847    8/2000
(Continued)

OTHER PUBLICATIONS

Duraiswamy et al., "Build a UWB pulse generator on an FPGA," EDN Network, Jun. 23, 2011; 2 pages.
(Continued)

*Primary Examiner* — Fredrick C Conley
(74) *Attorney, Agent, or Firm* — Barnes & Thornburg LLP

(57) ABSTRACT

A patient immersion sensor includes a radio detection and ranging (RADAR) apparatus to determine a time of flight (TOF) of a RADAR pulse and a reflected signal that is reflected by a patient or by a portion of a patient support surface supporting the patient. The TOF is indicative of an immersion depth or a distance toward bottoming out of a patient supported on the patient support surface, such as a mattress or a pad. The RADAR apparatus emits pulses of very short duration so as to be able to detect objects, such as a patient or a portion of a mattress or pad, at very close distances. The RADAR apparatus may use time-of-flight (TOF) between transmission of the pulse and receipt of a reflected signal to determine a distance toward bottoming out by the patient, thereby to determine if the patient is properly immersed into the patient support surface. Adjustments to inflation or deflation of one or more bladders are made to achieve a desired immersion amount within a tolerance range between upper and lower TOF thresholds.

22 Claims, 12 Drawing Sheets

Related U.S. Application Data continuation of application No. 16/018,316, filed on Jun. 26, 2018, now Pat. No. 10,813,809.

(60) Provisional application No. 62/645,495, filed on Mar. 20, 2018, provisional application No. 62/531,440, filed on Jul. 12, 2017.

(51) Int. Cl.

| | | |
|---|---|---|
| *A61B 5/00* | (2006.01) | |
| *A61B 5/0507* | (2021.01) | |
| *A61G 7/057* | (2006.01) | |
| *G01S 7/03* | (2006.01) | |
| *G01S 13/58* | (2006.01) | |
| *H01Q 1/22* | (2006.01) | |
| *H01Q 9/27* | (2006.01) | |
| *A61B 5/024* | (2006.01) | |
| *A61B 5/08* | (2006.01) | |
| *G01B 7/02* | (2006.01) | |
| *G01S 7/35* | (2006.01) | |
| *G01S 13/02* | (2006.01) | |
| *G01S 13/88* | (2006.01) | |

(52) U.S. Cl.
CPC ............ *A61B 5/6894* (2013.01); *G01S 7/032* (2013.01); *G01S 13/582* (2013.01); *H01Q 1/2216* (2013.01); *H01Q 9/27* (2013.01); *A61B 5/024* (2013.01); *A61B 5/0816* (2013.01); *A61B 5/447* (2013.01); *A61B 5/6892* (2013.01); *A61G 2203/20* (2013.01); *A61G 2203/34* (2013.01); *A61G 2203/40* (2013.01); *A61G 2203/44* (2013.01); *G01B 7/023* (2013.01); *G01S 7/358* (2021.05); *G01S 2013/0245* (2013.01); *G01S 13/88* (2013.01)

(58) Field of Classification Search
CPC ............ A61G 2203/40; A61G 2203/44; A47C 27/083; A61B 5/0507; A61B 5/6894; A61B 5/024; A61B 5/0816; A61B 5/447; A61B 5/6892; G01S 7/032; G01S 13/582; G01S 7/358; G01S 13/88; G01S 2013/0245; H01Q 1/2216; H01Q 9/27; G01B 7/023

See application file for complete search history.

(56) References Cited

U.S. PATENT DOCUMENTS

| | | |
|---|---|---|
| 5,625,914 A | 5/1997 | Schwab |
| 5,963,130 A | 10/1999 | Schlager et al. |
| 6,009,580 A | 1/2000 | Caminade et al. |
| 6,034,526 A | 3/2000 | Montant et al. |
| 6,079,068 A | 6/2000 | Viard |
| 6,244,272 B1 | 6/2001 | Montant et al. |
| 6,518,889 B2 | 2/2003 | Schlager et al. |
| 6,560,804 B2 | 5/2003 | Wise et al. |
| 7,515,059 B2 | 4/2009 | Price et al. |
| 7,676,872 B2 | 3/2010 | Block et al. |
| 7,973,666 B2 | 7/2011 | Petrosenko et al. |
| 8,026,840 B2 | 9/2011 | Dwelly et al. |
| 8,281,433 B2 | 10/2012 | Riley et al. |
| 8,352,015 B2 | 1/2013 | Bernstein et al. |
| 8,428,696 B2 | 4/2013 | Foo |
| 8,454,528 B2 | 6/2013 | Yuen et al. |
| 8,525,679 B2 | 9/2013 | Riley et al. |
| 8,740,793 B2 | 6/2014 | Cuddihy et al. |
| 8,750,971 B2 | 6/2014 | Tran |
| 8,781,563 B2 | 7/2014 | Foo |
| 9,002,427 B2 | 4/2015 | Tupin, Jr. et al. |
| 9,022,032 B2 | 5/2015 | Holzrichter |
| 9,468,307 B2 | 10/2016 | Lafleche et al. |
| 9,526,437 B2 | 12/2016 | Tupin, Jr. et al. |
| 9,549,691 B2 | 1/2017 | Tran |
| 9,775,758 B2 | 10/2017 | Riley et al. |
| 9,993,166 B1 | 6/2018 | Johnson et al. |
| 10,813,809 B2 | 10/2020 | Sauser et al. |
| 11,253,411 B2 | 2/2022 | Sauser et al. |
| 2008/0077015 A1* | 3/2008 | Boric-Lubecke ..... G01S 13/888 600/453 |
| 2009/0227882 A1* | 9/2009 | Foo ...................... A61B 5/7207 343/893 |
| 2010/0069745 A1* | 3/2010 | Muehlsteff ........... A61B 5/1107 600/425 |
| 2010/0152600 A1 | 6/2010 | Droitcour et al. |
| 2010/0240999 A1 | 9/2010 | Droitcour et al. |
| 2010/0249630 A1 | 9/2010 | Droitcour et al. |
| 2010/0249633 A1 | 9/2010 | Droitcour et al. |
| 2010/0292559 A1* | 11/2010 | Hannemann ............ G01S 13/88 600/407 |
| 2010/0292568 A1 | 11/2010 | Droitcour et al. |
| 2011/0102181 A1* | 5/2011 | Metz ..................... A61B 5/1115 340/575 |
| 2011/0263950 A1* | 10/2011 | Larson ................. A61B 5/6892 600/595 |
| 2011/0285579 A1 | 11/2011 | Bangera et al. |
| 2011/0296624 A1 | 12/2011 | Lafleche et al. |
| 2012/0212366 A1 | 8/2012 | Alalusi |
| 2012/0245479 A1 | 9/2012 | Ganesh et al. |
| 2013/0104312 A1 | 5/2013 | O'Reagan |
| 2013/0123614 A1 | 5/2013 | Bernstein et al. |
| 2013/0135137 A1 | 5/2013 | Mulder et al. |
| 2014/0059781 A1* | 3/2014 | Lafleche ............... A47C 27/083 5/713 |
| 2014/0235965 A1 | 8/2014 | Tran |
| 2015/0005675 A1 | 1/2015 | Riley et al. |
| 2015/0141794 A1 | 5/2015 | Foo |
| 2015/0181840 A1 | 7/2015 | Tupin, Jr. et al. |
| 2015/0208949 A1 | 7/2015 | Tupin, Jr. et al. |
| 2015/0223733 A1 | 8/2015 | Al-Alusi |
| 2015/0335310 A1 | 11/2015 | Bernstein et al. |
| 2015/0369911 A1 | 12/2015 | Mabrouk et al. |
| 2016/0022145 A1 | 1/2016 | Mostov |
| 2016/0022204 A1 | 1/2016 | Mostov |
| 2016/0213321 A1 | 7/2016 | Bernstein et al. |
| 2016/0228010 A1 | 8/2016 | Kim et al. |
| 2016/0317370 A1 | 11/2016 | Evans |
| 2017/0181409 A1 | 6/2017 | Tupin, Jr. et al. |
| 2017/0258366 A1 | 9/2017 | Tupin, Jr. et al. |
| 2017/0300650 A1 | 10/2017 | Margon |
| 2019/0015277 A1* | 1/2019 | Sauser .................. A61B 5/0507 |
| 2020/0107751 A1* | 4/2020 | Ghahremani ........... G01S 13/88 |
| 2021/0007921 A1 | 1/2021 | Sauser et al. |

FOREIGN PATENT DOCUMENTS

| | | |
|---|---|---|
| JP | 2008-536121 | 9/2008 |
| JP | 2010-508128 | 3/2010 |
| JP | 2013-538598 | 10/2013 |
| JP | 2014-209957 | 11/2014 |
| JP | 2015-528349 | 9/2015 |

OTHER PUBLICATIONS

Spiral Antennas, http://www.antenna-theory.com/antennas/travelling/spiral.php, Jun. 12, 2017; 7 pages.

Tapered Baluns, http://www.antenna-theory.com/definitions/taperedbalun.php, Jun. 12, 2017; 2 pages.

The Infinite Balun, http://www.antenna-theory.com/definitions/infinite.php, Jun. 12, 2017; 3 pages.

Minimal Measuring Range, http://www.radartutorial.eu/01.basics/Minimal%20Measuring%20Range.en.html; 1 page.

Yilmaz et al., "Ultra-Wideband N-Bit Digitally Tunable Pulse Generator," published in 2005 IEEE International Conference on Ultra-Wideband; Date of Conference Sep. 5-8, 2005; DOI: 10.1109/ICU.2005.1570027; 8 pages.

Notification of Reasons for Rejection for Japanese Patent Application No. 2018-127532 dated Aug. 27, 2019 and English translation; 6 pages.

(56) References Cited

OTHER PUBLICATIONS

Extended European Search Report for European Patent Application No. 18183006.8 dated Dec. 4, 2019; 9 pages.

* cited by examiner

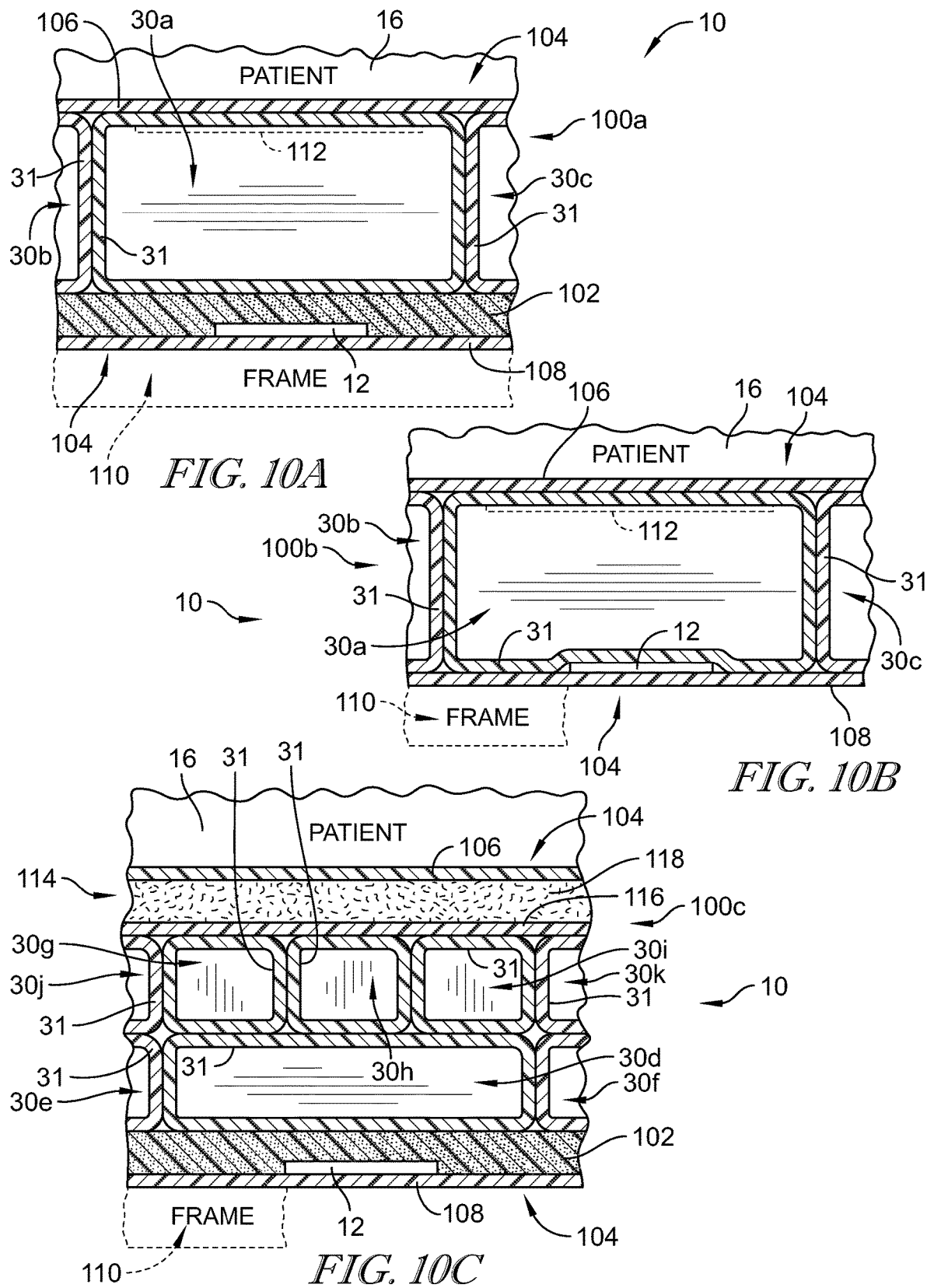

PATIENT SUPPORT APPARATUS HAVING A RADAR SYSTEM

The present application is a continuation of U.S. application Ser. No. 17/032,275, filed Sep. 25, 2020, now U.S. Pat. No. 11,253,411, which is a continuation of U.S. application Ser. No. 16/018,316, filed Jun. 26, 2018, now U.S. Pat. No. 10,813,809, which claims the benefit, under 35 U.S.C. § 119(e), of U.S. Provisional Application No. 62/531,440, filed Jul. 12, 2017, and U.S. Provisional Application No. 62/645,495, filed Mar. 20, 2018, each of which is hereby incorporated by reference herein in its entirety.

BACKGROUND

The present disclosure relates to patient support surfaces such as mattresses used on patient beds as well as pads used on chairs, stretchers, surgical tables, examination tables, and other types of patient support systems. More particularly the present disclosure relates to patient support surfaces having immersion sensors.

Patient support surfaces such as air mattresses and other types of patient support pads having sensors to determine an amount of immersion of a patient into the patient support surface are known. See, for example, U.S. Pat. Nos. 5,560,374; 6,009,580; 6,034,526; 6,079,068; 6,244,272; 6,560,804; and 9,468,307 in this regard. In general, the more a patient immerses into a mattress or pad, the greater the contact area between the patient and the support surface thereby reducing interface pressure between the patient and the support surface. Such prior art immersion sensors oftentimes rely upon principles of inductance and/or capacitance to measure a distance between upper and lower conductive sheets or coils. Having a conductive component at an upper surface of a mattress or lining the inside of an upper layer of a mattress with a conductive layer has a tendency to degrade the interface pressure performance of the mattress in the area of the conductive material. In some prior art embodiments, the conductive components are provided in a sublayer of a mattress that is beneath an upper air layer of the mattress and then assumptions are made as to the immersion depth of the patient based on an amount of compression of the sublayer.

In many of the prior art devices, the immersion sensors are located only in a seat region of a mattress beneath the patient's buttocks and are used to optimize the mattress inflation using a single measure of the patient immersion through the underlying air layer and/or, in some cases, foam layer. The risk of bottoming out increases as a head section of a bed frame is raised, for example, due to more of the patient's weight bearing downwardly through the buttocks onto the seat region of the mattress. In such prior art devices, the immersion depth of other portions of a patient's body, such as the head, shoulder blades, and heels, are not detected. Some prior art immersion detection devices have their components inside of air bladders of the mattress which introduces manufacturing complexities and expense to the mattress. Thus, a need exits for improvements in the use of sensors to detect patient immersion in patient support surfaces.

SUMMARY

An apparatus, system, or method may comprise one or more of the features recited in the appended claims and/or the following features which, alone or in any combination, may comprise patentable subject matter:

According to the present disclosure, a radio detection and ranging (RADAR) apparatus may be configured and may be operated to detect an object at a range of about 2 centimeters or less, although detection in the range of about 2 cm to about 100 cm is also contemplated. The RADAR apparatus may include at least one RADAR antenna and transceiver circuitry that may be coupled to the at least one RADAR antenna. The transceiver circuitry may cooperate with the at least one RADAR antenna to emit and subsequently receive a pulse that may have a profile that supports detection of the object at the range of about 2 centimeters. The RADAR apparatus may also have processor circuitry that may be configured to determine a time-of-flight (TOF) between transmission of the pulse and receipt by the at least one RADAR antenna of a reflected signal that may be reflected back from the object.

In some embodiments, the object may be comprised primarily of water. For example, the object may comprise a person. Alternatively or additionally, the object may comprise a reflective portion of a mattress. The portion may be a reflective layer or small reflective object, such as a piece of foil, metallic threads, etc.

In some embodiments, the at least one RADAR antenna may include at least one planar antenna. For example, the at least one planar antenna may include at least one spiral antenna to create a circularly polarized transmission. Alternatively or additionally, the at least one planar antenna may include at least one Archimedeal spiral broadband antenna. Further alternatively or additionally, the at least one planar antenna may include at least one log-periodic spiral broadband antenna. The at least one planar antenna may include at least one patch radiating element. The at least one planar antenna may include at least one radiating element.

The RADAR apparatus may further include impedance matching circuitry that may be configured to tune the at least one antenna to match an impedance of an environment through which the pulse and the reflected signal may travel. The environment may include at least a portion of a mattress, for example. The portion of the mattress may include at least one air bladder or may include multiple air bladders or may include at least one layer of foam or may include at least one microclimate management (MCM) layer or combinations of these bladders and layers. Alternatively or additionally, the environment may include a portion of a frame of a patient support system. The patient support system may include a bed, a chair, a wheelchair, a stretcher, a surgical table, an examination table, a patient lift, or an imaging apparatus. In some embodiments, the environment may include a portion of a frame of a patient support system and a portion of a mattress supported by the frame.

Optionally, the RADAR apparatus may further include an impedance-matched delay line that may be coupled to the impedance matching circuitry and to the at least one RADAR antenna. The impedance-matched delay line may increase an amount of time that it takes for the reflected signal to return to the impedance matching circuitry after the transmitted signal was generated thereby preventing interference between the emitted pulse and the reflected signal. The impedance-matched delay line may include, for example, one or more of the following: a radio frequency (RF) cable, a coaxial cable, an RF transmission line, an RF trace on a printed circuit board, a printed circuit board microstrip, or a waveguide.

The RADAR apparatus may further include at least one antenna feed to the at least one RADAR antenna and the at least one antenna feed may comprise a balun. The balun may comprise an infinite balun or a tapered balun, for example.

In some embodiments, the at least one antenna may include a transmitter antenna that emits the pulse and a receiver antenna that receives the reflected signal. Optionally, the transmitter antenna and the receiver antenna may be coupled to an integrated circuit chip that contains the transceiver circuitry and the processor circuitry. In some embodiments, the processor circuitry may determine a distance between the at least one antenna and the object based on averaging raw RADAR data of multiple reflected signals received over a period of time. Alternatively or additionally, the processor circuitry may determine a distance between the at least one antenna and the object based on multiple TOF determinations. For example, the distance d may be based on the formula TOF=2×d/c where c is the speed of light. Thus, d=TOF×c/2. In some embodiments, a measurement may be made that is linearly proportional to the distance. For example, to compensate for a slant range created by the spacing between the transmitter antenna and the receive antenna, the linear proportional distance may be d×cos(angle) or d×sin(angle) to convert the slant range into vertical distance if the transmitter antenna and receive antenna are looking at an angle toward the object.

In some embodiments, the processor circuitry may use pulse-pair processing to compare phases of successive reflected signals and to ignore any reflected signals that do not exhibit a phase shift from a prior reflected signal. Alternatively or additionally, the processor circuitry may use background subtraction to subtract data received when no object is present from the reflected signal received when the object is present. Optionally, the at least one RADAR antenna may include an array of RADAR antennae. For example, the array of RADAR antennae may include a phased-grid array of RADAR antennae.

In some embodiments, the processor circuitry may implement a Doppler filter to accept reflected signals within a desired frequency range and to reject other reflected signals. The Doppler filter may be configured as a band pass filter to accept reflected signals between a lower frequency threshold and an upper frequency threshold. Alternatively, the Doppler filter may be configured as a low pass filter to accept reflected signals that have a frequency less than a predetermined threshold. Further alternatively, the Doppler filter may be configured as a high pass filter to accept reflected signals that have a frequency greater than a predetermined threshold.

According to another aspect of the present disclosure, a method of reducing bedsores and improving clinical workflow may be provided. The method may include determining with a radio detection and ranging (RADAR) system a time-of-flight (TOF) or a distance from the patient to a bottom of a patient support system so as to maintain an immersion depth of the patient on the patient support system within a tolerance range that may achieve optimal interface pressure between the patient and the patient support system. The tolerance range may be based on upper and lower TOF thresholds, or upper and lower distance thresholds, or both.

In some embodiments, the method may include providing the TOF or distance to a remote server. If desired, the method may include adjusting the patient support system as a function of the TOF or distance. For example, adjusting the patient support system may include lowering a head section of a bed frame of the patient support system. Alternatively or additionally, adjusting the patient support system may include inflating or deflating a bladder of a mattress of the patient support system. The method may include notifying a clinician if the TOF or distance is less than a threshold.

In some embodiments, the method may include determining patient motion with the RADAR system. The method may further include providing patient motion information to the clinician. The method may include causing patient motion by changing inflation pressures of various bladders supporting the patient. Optionally, the method may include providing patient motion information to a remote server.

According to a further aspect of the present disclosure, a patient support system may include a patient support structure to support a patient, control circuitry that may be coupled to the patient support structure, and at least one radio detection and ranging (RADAR) apparatus that may be coupled to the patient support structure. The control circuitry may provide power to the at least one RADAR apparatus and may receive data from the at least one RADAR apparatus. The control circuitry may perform at least one function in response to the data that may be received from the at least one RADAR apparatus.

In some embodiments, the patient support structure may include one or more air bladders and the at least one function may include changing inflation of the one or more air bladders. The at least one RADAR apparatus may include at least one RADAR antenna and changing inflation of the one or more air bladder may include deflating the one or more air bladders to lessen a distance between the patient and the at least one RADAR antenna. Alternatively or additionally, the at least one RADAR apparatus may include at least one RADAR antenna and changing inflation of the one or more air bladder may include inflating the one or more air bladders to increase a distance between the patient and the at least one RADAR antenna.

The patient support system may include a server that may be separate from the patient support structure, the control circuitry, and the at least one RADAR apparatus and the at least one function may include transmitting the data to the server. In some embodiments, the server may aggregate the data received by the control circuitry from the at least one RADAR system and transmitted by the control circuitry along with position data relating to a position of one or more components of the patient support structure, demographic data relating to patient demographics, and bedsore data relating to clinical results of bedsores. The patient demographics may include one or more of the following: patient condition such as being of limited mortality, patient disease history, patient height, patient weight, or age of the patient.

In some embodiments, the at least one RADAR apparatus may be configured to determine a heart rate (HR) and a respiration rate (RR) of the patient. For example, the at least one RADAR apparatus may use Doppler shift information to determine the HR and the RR. Alternatively or additionally, the at least one RADAR apparatus may use ballistocardiography to determine the HR and the RR. Optionally, the at least one RADAR apparatus may detect chest movement due to a heartbeat of the patient to determine the HR. Optionally, the at least one RADAR apparatus detects diaphragm movement of the patient to determine the RR.

In some embodiments, the control circuitry may be configured to determine a heart rate (HR) and a respiration rate (RR) of the patient based on the data received from the at least one RADAR apparatus. For example, the control circuitry may use the data from the at least one RADAR apparatus to determine Doppler shift information to determine the HR and the RR. Alternatively or additionally, the control circuitry may use the data from the at least one RADAR apparatus to perform ballistocardiography to determine the HR and the RR. Optionally, the control circuitry may use the data from the at least one RADAR apparatus to detect chest movement due to a heartbeat of the patient to determine the HR. Optionally, the control circuitry may use the data from at least one RADAR apparatus to detect diaphragm movement of the patient to determine the RR.

According to yet another aspect of the present disclosure, a patient support system may include a mattress that may have a top surface and a bottom surface. The mattress may be configured to support a patient on the top surface. The patient support system may also have a radio detection and ranging (RADAR) apparatus that may be operable to measure information indicative of a risk of contracting a pressure ulcer due to improper immersion in at least one location of the mattress.

In some embodiments, the RADAR apparatus may include an array of RADAR antennae. The array of RADAR antennae may include a phased-grid array, for example. The array of RADAR antennae may include a static position, static phase, multiplexed array. If desired, at least one or more antennae of the array of RADAR antennae may be moved mechanically relative to the mattress.

In some embodiments, the patient support system may further include a frame to support the mattress and an antennae holder that may be movable relative to the frame beneath the bottom surface of the mattress. The one or more antennae may be carried by the antennae holder. The antennae holder may include a plate. The patient support system may include a guide that may be coupled to the frame and that may be configured to support the plate for movement relative to the frame. The patient support system may further include an actuator that may be operated to move the plate relative to the guide and relative to the frame. The actuator may include one or more of the following: a lead screw, a motor, a gear reducer, a linkage, a pulley, a sprocket, a cable, a belt, or a chain.

In some embodiments, a portion of the frame may serve as a guide to support the plate for movement. The patient support system may include an actuator that may be operated to move the plate relative to the portion of the frame that serves as the guide. The actuator may include one or more of the following: a lead screw, a motor, a gear reducer, a linkage, a pulley, a sprocket, a cable, a belt, or a chain.

It is within the scope of this disclosure for the one or more antennae carried by the antennae holder to include three antennae that may be situated and movable beneath a sacral region of the patient supported by the mattress. Alternatively or additionally, the one or more antennae carried by the antennae holder may include two antennae that may be situated and movable beneath a back region of the patient supported by the mattress. Alternatively or additionally, the one or more antennae carried by the antennae holder may include two antennae that may be situated and movable beneath a heel region of the patient supported by the mattress.

According to still a further aspect of the present disclosure, a patient support surface for supporting a patient may include a core that may include at least one patient support element and a ticking that may surround the core. The ticking may have an upper layer overlying the core and a lower layer underlying the core. The patient support surface may also have at least one radio detection and ranging (RADAR) antenna that may be situated beneath the core, such as between the lower layer of the ticking and the core or beneath both the lower layer of ticking and the core. The at least one RADAR antenna may emit a pulse that travels through the core and that may be reflected by either the patient or an inner surface of the upper layer of the ticking as a reflected signal back to the at least one RADAR antenna. The patient support surface also may include processor circuitry that may determine a time-of-flight (TOF) of the pulse and the reflected signal to determine whether the patient supported on the patient support surface is at risk of contracting pressure ulcers due to improper immersion into the patient support surface.

In some embodiments, the at least one RADAR antenna may include at least one planar antenna. For example, the at least one planar antenna may include at least one spiral antenna to create a circularly polarized transmission. Alternatively or additionally, the at least one planar antenna may include an Archimedeal spiral broadband antenna. Alternatively or additionally, the at least one planar antenna may include a log-periodic spiral broadband antenna.

In some embodiments, the patient support surface may further include an impedance matching circuit that may be configured to tune the at least one antenna to match an impedance of the core. The patient support surface may include at least one antenna feed to the at least one RADAR antenna. The at least one antenna feed may comprise a balun. The balun may comprise an infinite balun or a tapered balun, for example. The patient support surface may include at least one radio frequency (RF) driver circuit and the balun may be configured to provide impedance matching from the at least on RF driver circuit to the at least one RADAR antenna. Other impedance matching circuits, such as a PI filter may be used. Such a matching filter may be implemented using discrete components or transmission line elements.

In some embodiments, the patient support surface may include driver circuitry that may be coupled to the at least one RADAR antenna. Optionally, the driver circuitry may cooperate with the at least one RADAR antenna to emit a pulse that may have a period in the range of about 0.55 nanoseconds (ns) to about 0.2 ns which are pulse lengths typical of ultra-wide band (UWB) pulses. Such a short pulse may permit objects within 2 centimeters of the at least one RADAR antenna to be detected.

In some embodiments, the patient support surface may include impedance matching circuitry that may be configured to tune the at least one RADAR antenna to match an impedance of an environment through which the pulse and the reflected signal travel. The environment may include at least a portion of the at least one patient support element of the core and a portion of the ticking, for example. The at least one patient support element may include an air bladder or multiple air bladders. Alternatively or additionally, the at least one patient support element may include at least one layer of foam. The environment may include a portion of a panel that supports at least a portion of the patient support surface or a portion of a frame of a patient support system that supports the patient support surface. For example, the patient support system may include a bed, a chair, a wheelchair, a stretcher, a surgical table, an examination table, a patient lift, or an imaging apparatus. If desired, the inner surface of the upper layer of ticking may have a RADAR reflective coating.

Optionally, the patient support surface may further include an impedance-matched delay line that may be coupled to the impedance matching circuitry and to the at least one RADAR antenna. The impedance-matched delay line may increase an amount of time that it takes for the reflected signal to reach the impedance matching circuitry thereby preventing interference between the emitted pulse and the reflected signal. The impedance-matched delay line may include, for example, one or more of the following: a radio frequency (RF) cable, a coaxial cable, an RF transmission line, an RF trace on a printed circuit board, a printed circuit board microstrip, or a waveguide.

This disclosure contemplates that the at least one antenna may include a transmitter antenna that may emit the pulse and a receiver antenna that may receive the reflected signal. In some embodiments, the transmitter antenna and the receiver antenna may be coupled to an integrated circuit that may contain the driver circuitry and the processor circuitry. Optionally, the transmitter antenna and the receiver antenna may be coupled to an integrated circuit chip by impedance matching circuitry. Such an integrated circuit chip may include the driver circuitry or the processor circuitry or both.

In some embodiment, the processor circuitry may use TOF to determine a distance based on averaging raw RADAR data of multiple reflected signals received over a period of time. Alternatively or additionally, the processor circuitry may determine a distance based on multiple TOF determinations. In some embodiments, the processor circuitry may use pulse-pair processing to compare phases of successive reflected signals and to ignore any reflected signals that do not exhibit a phase shift from a prior reflected signal. Alternatively or additionally, the processor circuitry may use background subtraction to subtract data received when no patient is present on the patient support surface from the reflected signal received when the patient is present.

In some embodiments of the patient support surface, the at least one RADAR antenna may include an array of RADAR antennae. The array of RADAR antennae may include a phased-grid array of antennae, for example. If desired, the processor circuitry may implement a Doppler filter to accept reflected signals within a desired frequency range and to reject other reflected signals. The Doppler filter may be configured as a band pass filter to accept reflected signals between a lower frequency threshold and an upper frequency threshold. Alternatively, the Doppler filter may be configured as a low pass filter to accept reflected signals that have a frequency less than a predetermined threshold. Further alternatively, the Doppler filter may be configured as a high pass filter to accept reflected signals that have a frequency greater than a predetermined threshold.

In some embodiment, the core may include one or more air bladders and wherein inflation of the one or more air bladders is changed in response to the TOF. For example, the one or more air bladders may be changed via deflation to lessen the TOF. The one or more air bladders may be changed via inflation to increase the TOF. Thus, the TOF may be controlled within a range to prevent the patient from bottoming out but also to permit the patient to immerse into the patient support surface sufficiently to reduce interface pressures.

In some embodiments, the processor circuitry of the patient support surface may be configured to determine a heart rate (HR) and a respiration rate (RR) of the patient based on the TOF of successive pulses. The processor circuitry may use Doppler shift information to determine the HR and the RR. Alternatively or additionally, the processor circuitry may use ballistocardiography to determine the HR and the RR. If desired, the processor circuitry may detect chest movement due to a heartbeat of the patient to determine the HR. Alternatively or additionally, the processor circuitry may detect diaphragm movement of the patient to determine the RR.

According to yet a further aspect of the present disclosure, a patient support system for supporting a patient may include a mattress that may include a core and a ticking that may surround the core. The ticking may have an upper layer overlying the core and a lower layer underlying the core. The patient support system may have a frame that may include a mattress support deck that may support the mattress. At least one radio detection and ranging (RADAR) antenna may be coupled to the frame beneath the lower layer of ticking. The at least one RADAR antenna may emit a pulse that may travel through the mattress and that may be reflected by either the patient or an inner surface of the upper layer of the ticking or a portion of an inner surface of the upper layer of the ticking (e.g. reflective threads or patches) as a reflected signal back to the at least one RADAR antenna. The patient support system may have processor circuitry that may determine a time-of-flight (TOF) of the pulse and the reflected signal to determine whether the patient supported on the patient support surface may be at risk of bottoming out.

In some embodiments, the mattress support deck may include a plurality of deck sections and the at least one RADAR antenna may be coupled to an upper surface of a first deck section of the plurality of deck sections. Alternatively or additionally, the mattress support deck may include a plurality of deck sections and the at least one RADAR antenna may be coupled to a bottom surface of a first deck section of the plurality of deck sections. Thus, the pulse may travel through the first deck section and the mattress.

In some embodiments, the at least one RADAR antenna of the patient support system may include at least one planar antenna. The at least one planar antenna may include, for example, at least one spiral antenna to create a circularly polarized transmission. The at least one planar antenna may include an Archimedeal spiral broadband antenna. Alternatively or additionally, the at least one planar antenna may include a log-periodic spiral broadband antenna.

It is within the scope of this disclosure for the patient support system to include an impedance matching circuit that may be configured to tune the at least one RADAR antenna to match an impedance of the a portion of the mattress through which the pulse and the reflected signal travel. It is also within the scope of this disclosure for the patient support system to include an impedance matching circuit configured to tune the at least one RADAR antenna to match an impedance of the mattress and a portion of the frame through which the pulse and the reflected signal travel.

In some embodiments, the patient support system may include at least one antenna feed to the at least one RADAR antenna and the at least one antenna feed may include a balun. The balun may include an infinite balun or a tapered balun, for example. The patient support system may include at least one radio frequency (RF) driver circuit and the balun may be configured to provide impedance matching from the at least on RF driver circuit to the at least one RADAR antenna.

Optionally, the patient support system may further include an impedance-matched delay line that may be coupled to the impedance matching circuitry and to the at least one RADAR antenna. The impedance-matched delay line may increase an amount of time that it takes for the reflected signal to reach the impedance matching circuitry thereby preventing interference between the emitted pulse and the reflected signal. The impedance-matched delay line may include, for example, one or more of the following: a radio frequency (RF) cable, a coaxial cable, an RF transmission line, an RF trace on a printed circuit board, a printed circuit board microstrip, or a waveguide.

In some embodiments of the patient support system, an inner surface of the upper layer of ticking may have a RADAR reflective coating. If desired, the core may include an air bladder. Alternatively or additionally, the core may include multiple air bladders with at least a first air bladder situated above a second air bladder. Alternatively or additionally, the core may include at least one layer of foam.

It is contemplated by this disclosure that the at least one antenna may include a transmitter antenna that may emit the pulse and a receiver antenna that may receive the reflected signal. The transmitter antenna and the receiver antenna may be coupled to an integrated circuit that may contain driver circuitry and the processor circuitry. The processor circuitry may determine a distance between the at least one antenna and the patient based on averaging raw RADAR data of multiple reflected signals received over a period of time. Alternatively or additionally, the processor circuitry may determine a distance between the at least one antenna and the patient based on multiple TOF determinations.

The processor circuitry of the patient support system may use pulse-pair processing to compare phases of successive reflected signals and to ignore any reflected signals that do not exhibit a phase shift from a prior reflected signal. Alternatively or additionally, the processor circuitry may use background subtraction to subtract data received when no patient is present on the mattress from the reflected signal received when the patient is present on the mattress. The at least one RADAR antenna may comprise an array of RADAR antennae. The array of RADAR antennae may include a phased-grid array of antennae.

In some embodiments, the processor may implement a Doppler filter to accept reflected signals within a desired frequency range and to reject other reflected signals. The Doppler filter may be configured as a band pass filter to accept reflected signals between a lower frequency threshold and an upper frequency threshold. The Doppler filter may be configured as a low pass filter to accept reflected signals that have a frequency less than a predetermined threshold. The Doppler filter may be configured as a high pass filter to accept reflected signals that have a frequency greater than a predetermined threshold.

In some embodiments of the patient support system, the core may include one or more air bladders and inflation of the one or more air bladders may be changed in response to the TOF. For example, the one or more air bladders may be changed via deflation to permit the patient to further immerse into the mattress. The one or more air bladders may be changed via inflation to decrease the risk of the patient bottoming out.

In some embodiments of the patient support system, the processor circuitry may be configured to determine a heart rate (HR) and a respiration rate (RR) of the patient based on the TOF of successive pulses. The processor circuitry may use Doppler shift information to determine the HR and the RR, for example. Alternatively or additionally, the processor circuitry may use ballistocardiography to determine the HR and the RR. The processor circuitry may detect chest movement due to a heartbeat of the patient to determine the HR. The processor circuitry may detect diaphragm movement of the patient to determine the RR.

According to another aspect of the present disclosure, a patient support surface may include a ticking that may define an interior region between a top layer of the ticking and a bottom layer of the ticking. At least one layer of foam material may fill the interior region. A radio detection and ranging (RADAR) apparatus may be operable to measure a distance toward bottoming out of a patient on the mattress. The RADAR apparatus may include at least one RADAR antenna. Processor circuitry may be provided to determine whether the performance of the at least one layer of foam material has degraded based on the distance, or based on the distance and patient weight.

In some embodiments, the processor circuitry may provide an alert if the degradation indicates that a useful life of the patient support surface has been reached.

According to a further aspect of the present disclosure, a patient support surface may include a ticking that may define an interior region between a top layer of the ticking and a bottom layer of the ticking. At least one layer of foam material may fill the interior region. A radio detection and ranging (RADAR) apparatus may have at least one RADAR antenna that may emit a pulse that may travel through the foam material and that may be reflected by either the patient or an inner surface of the top layer of the ticking as a reflected signal back to the at least one RADAR antenna. Processor circuitry may be provided to determine a time-of-flight (TOF) of the pulse and the reflected signal. The processor circuitry may also determine an amount of degradation of the foam material based on the TOF and based on patient weight.

In some embodiments, the processor circuitry may provide an alert if the amount of degradation exceeds a threshold indicating that a useful life of the patient support surface has been reached.

According to still another aspect of the present disclosure, a patient support system may include a mattress that may have a top surface and a bottom surface. The mattress may be configured to support a patient on the top surface. A radio detection and ranging (RADAR) apparatus may have at least one RADAR antenna that may emit a pulse that may travel through the mattress and that may be reflected by either the patient or an inner surface of a material defining the top surface as a reflected signal back to the at least one RADAR antenna. Processor circuitry may determine a time-of-flight (TOF) of the pulse and the reflected signal. The patient support system may have a frame to support the mattress. An antenna holder may be movable relative to the frame beneath the bottom surface of the mattress. The at least one antenna may be carried by the antenna holder.

In some embodiments, the antenna holder may include a plate. The patient support system may include a guide that may be coupled to the frame and that may be configured to support the plate for movement relative to the frame. The patient support system may further include an actuator that may be operated to move the plate relative to the guide and relative to the frame. The actuator may include one or more of the following: a lead screw, a motor, a gear reducer, a linkage, a pulley, a sprocket, a cable, a belt, or a chain.

In some embodiments, a portion of the frame may serve as a guide to support the plate for movement. The patient support system may include an actuator that may be operated to move the plate relative to the portion of the frame that serves as the guide. The actuator may include one or more of the following: a lead screw, a motor, a gear reducer, a linkage, a pulley, a sprocket, a cable, a belt, or a chain.

In some embodiments, the at least one antenna carried by the antenna holder may include three antennae that may be situated and movable beneath a sacral region of the patient supported by the mattress. Alternatively or additionally, the at least one antenna carried by the antenna holder may include two antennae that may be situated and movable beneath a back region of the patient supported by the mattress. Alternatively or additionally, the at least one antenna carried by the antenna holder may include two antennae that may be situated and movable beneath a heel region of the patient supported by the mattress.

According to still a further aspect of the present disclosure, a patient support apparatus may include a frame, a mattress that may be supported by the frame, and an immersion sensor that may be coupled to the frame and that may be located outside of the mattress. The immersion sensor may be operable to determine patient immersion into an upper surface of the mattress.

In some embodiments, the immersion sensor may be located underneath the mattress. The immersion sensor may include a radio detection and ranging (RADAR) antenna and a bottom surface of the mattress may abut an upper surface of the RADAR antenna. Optionally, the RADAR antenna may include a housing and a portion of the housing may provide the upper surface. The frame may include a mattress support deck that may include at least one pivotable deck section and the RADAR antenna may be situated atop the pivotable deck section.

In some embodiments, the frame may include a mattress support deck that may include at least one pivotable deck section and the immersion sensor may include a radio detection and ranging (RADAR) antenna that may be located beneath the pivotable deck section. For example, the RADAR antenna may be coupled to a bottom surface of the pivotable deck section.

In some embodiments, the frame may include an antenna holder that may be located beneath a bottom surface of the pivotable deck section and the RADAR antenna may be carried by the antenna holder. If desired, the antenna holder may include a plate. The pivotable deck section may include a guide that may be configured to support the plate for movement relative to the pivotable deck section. The patient support apparatus may further include an actuator that may be operated to move the plate. The actuator may include one or more of the following: a lead screw, a motor, a gear reducer, a linkage, a pulley, a sprocket, a cable, a belt, or a chain.

As contemplated by some embodiments of this disclosure, the immersion sensor may include a radio detection and ranging (RADAR) antenna, radio frequency (RF) driver and receiver circuitry, impedance matching circuitry that may be coupled to the RADAR antenna and that may be coupled to the RF driver and receiver circuitry, and processor circuitry that may be coupled to the RF driver and receiver circuitry.

Optionally, the patient support apparatus may further include an impedance-matched delay line that may be coupled to the impedance matching circuitry and to the RADAR antenna. The impedance-matched delay line may increase an amount of time that it takes for a reflected signal to reach the impedance matching circuitry thereby preventing interference between an emitted pulse and the reflected signal. The impedance-matched delay line may include, for example, one or more of the following: a radio frequency (RF) cable, a coaxial cable, an RF transmission line, an RF trace on a printed circuit board, a printed circuit board microstrip, or a waveguide.

According to yet another aspect of the present disclosure, a system for detecting time of flight in a patient support system may be provided. The system may include a patient support (bed, chair, table, stretcher, etc), a RADAR that may be integrated into the patient support, an antenna, and an algorithm for determining the time between transmission and reception of a RADAR pulse.

According to still a further aspect of the present disclosure, a mattress end-of-life testing apparatus for use with a mattress may be provided. The mattress end-of-life testing apparatus may include at least one RADAR antenna that may be placed beneath the mattress, at least one test weight that may be placed atop the mattress, and circuitry that may be coupled to the at least on RADAR antenna and that may have an algorithm for determining an amount of time between transmission and reception of a RADAR pulse. The amount of time may be used to determine whether the mattress has reached an end of its useful life.

According to yet still another aspect of the present disclosure, a patient support apparatus may include a patient support frame, a patient support surface that may be supported on the patient support frame, and a RADAR system that may be carried by the patient support frame, that may be operable to determine a depth to which a patient is immersed into the patient support surface, and that may be operable to perform a Doppler analysis to determine at least one of a heart rate or a respiration rate of the patient.

In some embodiments, the RADAR system may be operable to determine both the heart rate and respiration rate of the patient. The RADAR system may include electronically steerable RADAR sensors, for example. The electronically steerable RADAR sensors, in turn, may include a plurality of transmitting antennae and a plurality of receiving antennae. The plurality of transmitting antennae and the plurality of receiving antennae may be arranged in a grid beneath an upper surface of the patient support surface. Reflected signals from the plurality of transmitting antennae may be combined to improve signal-to-noise ratio, change the gain, steer the direction of the beam, and/or to allow scanning of a larger area.

In some embodiments, signals received by the plurality of receiving antennae may be used by the RADAR system for body contour mapping. The body contour mapping may be used to determine whether the patient is at risk of developing pressure ulcers. Alternatively or additionally, the body contour mapping may be used in connection with determining a Braden score for the patient including determining a patient mobility sub-factor of the Braden score. Micromotion for the patient may be determined using, for example, Doppler processing. Further alternatively or additionally, the body contour mapping may be used in connection with determining functional decline of the patient. Still further alternatively or additionally, the body contour mapping may be used to determine a location on the patient support surface of at least one of the patient's legs, arms, trunk, pelvis or head.

Optionally, the body contour mapping may be used to determine whether the patient is side-lying, lying on their stomach, or lying on their back. The patient support surface may include one or more air bladders and inflation of at least one air bladder of the one or more air bladders may be adjusted based on whether the patient is side-lying, lying on their stomach, or lying on their back. Alternatively or additionally, the body contour mapping may be used to determine whether the patient has slid toward a foot end of the patient support surface. The patient support surface may include one or more air bladders and inflation of at least one air bladder of the one or more air bladders may be adjusted based on whether the patient has slid toward the foot end of the patient support surface or whether the patient is in a proper position on the patient support apparatus. If desired, the body contour mapping may be used to determine sleep quality of the patient, for example by analyzing movement and/or respiration. Alternatively or additionally, the body contour mapping may be used to determine impending exit of the patient from the patient support apparatus.

In some embodiments, the RADAR system may be operable to determine a distance to the patient or to a surface of the patient support surface adjacent the patient for each receiving antenna of the plurality of receiving antennae by using (i) a time-of-flight (TOF) between transmission of pulses from the plurality of transmitting antennae and receipt by the plurality of receiving antennae of a reflected signal that is reflected back from the patient or reflected back from the surface of the patient support surface adjacent the patient, (ii) antenna beam angle and geometry, and (iii) signal strength.

The present disclosure contemplates that the Doppler analysis to determine at least one of a heart rate or a respiration rate of the patient may include a micro-Doppler analysis that may determine a phase change between first signals that may be transmitted by the plurality of transmitting antennae and second signals that may be received by the plurality of receiving antennae. The Doppler analysis may be used to determine one or more of the following: premature ventricular contractions (PVC's) of the patient's heart; rate-based arrhythmias of the patient's heart; lethal arrhythmias of the patient's heart; onset of congestive heart failure; or progression of congestive heart failure. Alternatively or additionally, the Doppler analysis may be used to detect apnea and/or obstructive sleep apnea of the patient.

In some embodiments, the RADAR system may include a local oscillator, a power splitter that may have an input coupled to the local oscillator, and at least one transmitting antenna that may be coupled to a first output of the power splitter. The RADAR system may further have a mixer that may include a first input that may be coupled to a second output of the power splitter and at least one receiving antenna that may be coupled to a second input of the mixer. A first low pass filter of the RADAR system may have an input that may be coupled to a quadrature output of the mixer and a second low pass filter of the RADAR system may have an input that may be coupled to an in-phase output of the mixer. The RADAR system may further have a first analog-to-digital converter that may be coupled to an output of the first low pass filter and a second analog-to-digital converter that may be coupled to an output of the second low pass filter. It is contemplated by this disclosure that the RADAR system may be instantiated as a system-on-chip.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which:

FIG. 10A is a cross sectional view showing a portion of an air mattress, a portion of a patient supported by the air mattress, and a portion of a frame (in phantom) of a patient support apparatus that supports the air mattress, the air mattress having a RADAR antenna sandwiched between a bottom ticking layer of the air mattress and a base foam layer of the air mattress, an inflatable bladder above the base foam layer, and a top layer of ticking between the inflatable air bladder and the patient, and also showing an optional RADAR reflective coating (in phantom) on an inside surface at a top of the inflatable air bladder;

FIG. 10B is a cross sectional view, similar to FIG. 10A but having the foam layer removed, showing that the RADAR antenna is sandwiched between the bottom ticking layer and the inflatable bladder resulting in a mattress of reduced vertical thickness as compared to the mattress of FIG. 12A;

FIG. 10C is a cross sectional view, similar to FIG. 10A, showing an alternative embodiment of a mattress having a lower inflatable air bladder situated atop the base foam layer, a set of three upper bladders situated atop the lower inflatable bladder, and a microclimate management layer above the upper bladders;

DETAILED DESCRIPTION

According to some embodiments of the present disclosure, one or more radio detection and ranging (RADAR) apparatuses are integrated into a patient support system and are used to determine patient immersion, or stated more accurately, to determine a risk of a patient bottoming out on a patient support surface of the patient support system. The RADAR apparatuses disclosed herein measure a time-of-flight (TOF) of a RADAR pulse which, if desired, can be used to calculate a distance between at least one RADAR antenna and an object of interest, such as the patient. The TOF or distance is used in some contemplated embodiments to control bladder inflation and deflation to maintain the patient within a desired immersion depth between upper and lower tolerance range limits. The tolerance range limits are upper and lower TOF thresholds, or upper and lower distance thresholds, or both. By maintaining the patient at the desired immersion depth, while preventing bottoming out of the patient, the interface pressure between the patient and the surface supporting the patient is maintained at optimum values.

While all types of patient support systems are contemplated herein, some examples of a patient support system include a standalone mattress system, a mattress overlay, a patient bed, a patient bed with an integrated mattress system, a surgical table, an examination table, an imaging table, a stretcher, a chair, a wheelchair, and a patient lift, just to name a few. Patient support surfaces contemplated herein include air mattress, foam mattresses, combination air and foam mattresses, mattress overlays, surgical table pads and mattresses, stretcher pads and mattresses, chair pads, wheelchair pads, and patient lift pads, just to name a few.

Figure 1:
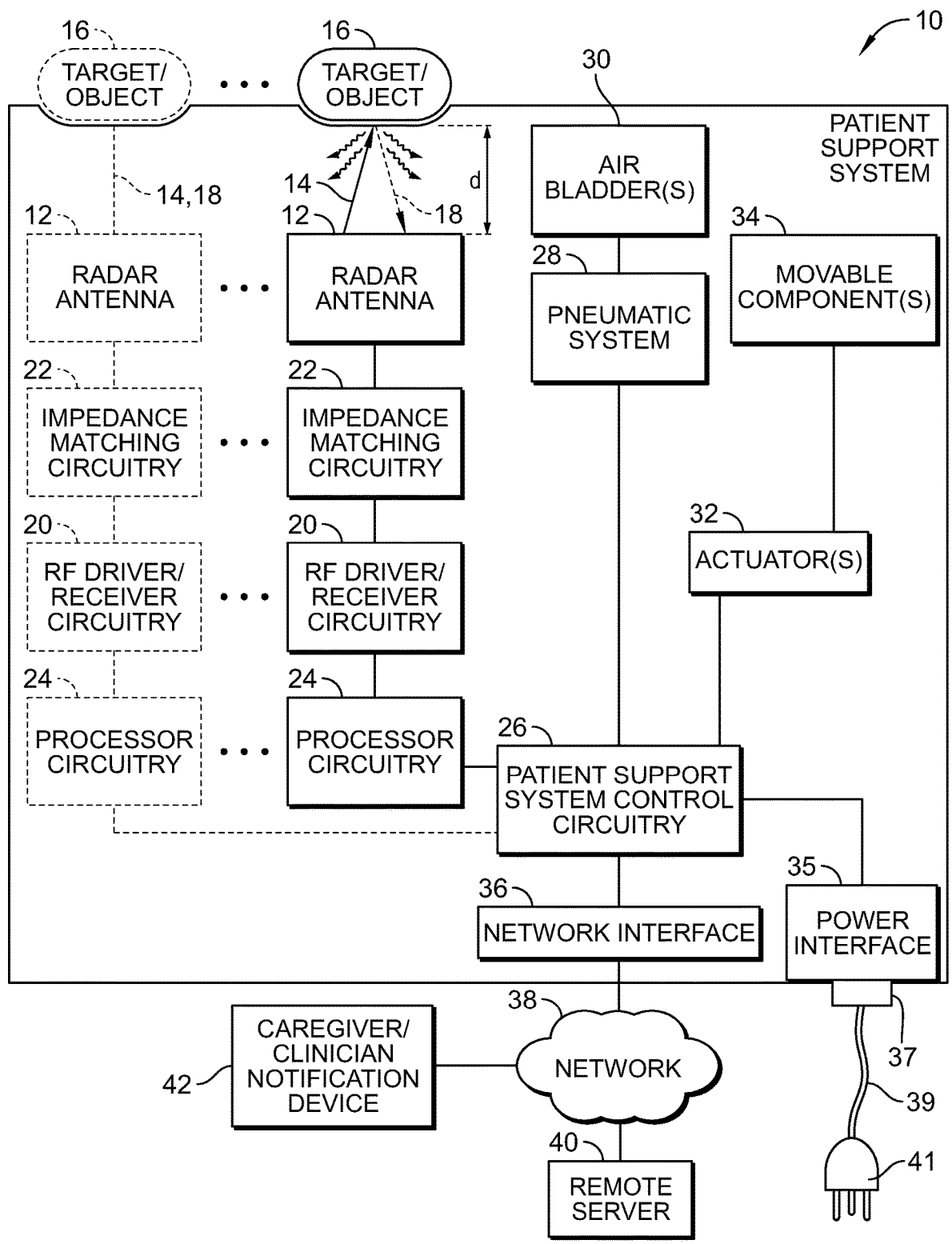
FIG. 1 is a block diagram showing a patient support system having a radio detection and ranging (RADAR) apparatus integrated therein (in solid) and having one or more optional additional RADAR apparatuses integrated therein (in phantom); the RADAR apparatus including a RADAR antenna, impedance matching circuitry, RF driver/receiver circuitry, and processor circuitry; the RADAR apparatus coupled to control circuitry which signals a pneumatic system to adjust inflation of one or more air bladders and/or which signals one or more actuators to move movable portions of the patient support system based on a distance, d, or a time-of-flight of a pulse and return signal, between the RADAR antenna and an object or target as determined by the RADAR apparatus.

As shown diagrammatically in FIG. 1, a patient support system 10 includes one or more RADAR antenna 12 which are operated to emit a pulse 14 generally upwardly toward a target or object 16. In some embodiments, the object 16 is a patient situated atop a patient support surface, such as a mattress or pad, of the patient support system 10. Patients are comprised primarily of water. The pulse 14 is reflected by the object 16 as a reflected signal 18 which is detected or read by RADAR antenna 12. Losses, such as absorbed and refracted energy, are indicated diagrammatically in FIG. 1 with squiggly arrows.

Patient support system 10 includes radio frequency (RF) driver and receiver circuitry 20 coupled to each respective RADAR antenna 12 by corresponding impedance matching circuitry 22 as shown diagrammatically in FIG. 1. RF driver/receiver circuitry is sometimes referred to herein as RF transceiver circuitry. The RF driver portion of circuitry 20 operates to provide a pulse of electrical energy (i.e., current and voltage) via impedance matching circuitry 22 to cause the RADAR antenna 12 to emit the pulse 14. The receiver portion of circuitry 20 receives the reflected signal 18 from RADAR antenna 12 via impedance matching circuitry 22.

Patient support system also includes processor circuitry 24 coupled to respective RF driver/receiver circuitry 20. One or more of RADAR antenna 12 and circuitry 20, 22, 24 is considered to be a RADAR apparatus or RADAR system according to this disclosure. In some embodiments, the receiver portion of circuitry 20 or the processor circuitry 24 includes an analog-to-digital converter (ADC) to convert the received analog reflected signal 18 into digital data. In some embodiments, circuitry 20 sends to processor circuitry 24 data indicative of a time-of-transmission of pulse 14 and a time-of-arrival of reflected signal 18 by RADAR antenna 12. The difference between the time-of-transmission and time-of-arrival is the time-of-flight (TOF) of pulse 14 and signal 18. The TOF is determined by processor 24 in some embodiments and is determined by circuitry 20 in other embodiments. In those embodiments in which circuitry 20 calculates the TOF, it is output to processor circuitry 24 from circuitry 20.

Processor circuitry 24 uses the TOF data to determine whether the object, sometimes referred to herein as "the patient 16," is at risk of bottoming out. Bottoming out, sometimes referred to herein as just "bottoming," refers to a condition in which a patient or other weight on top of a mattress or pad compresses the top of the mattress or pad until it reaches its lowest point, i.e., it cannot be compressed any farther. At that point, there is little to no further cushioning and the mattress or pad would feel hard and uncomfortable to the patient. Thus, the risk for the patient 16 to develop pressure ulcers increases greatly if the patient bottoms out on a mattress or pad. Alternatively or additionally, processor circuitry 24 uses the TOF data to set or adjust bladder pressures for optimal immersion of the patient into the mattress or pad to reduce interface pressure (IFP) between the patient and the upper surface of the mattress or pad. The optimal immersion is considered to occur if the TOF data is within a tolerance range between upper and lower TOF thresholds.

In some embodiments, the TOF data may be used directly by processor circuitry 24 to determine whether the patient is at risk of bottoming out. In such embodiments, the TOF data is compared to a TOF threshold to make the determination. In other embodiments, a distance, d, shown in FIG. 1, between RADAR antenna 12 and the patient 16 is calculated based on the TOF and then the distance, d, is compared to a distance threshold. The TOF and distance, d, are related mathematically in that TOF=2×d/c where c is the speed of light. Thus, d=TOF×c/2. Thus, TOF or distance, d, can be compared to a threshold to determine how close the patient 16 is to bottoming out.

According to this disclosure, the pulse 14 is very short in duration so that patients within about 2 centimeters (cm) or less of bottoming out can be detected. Of course, at the option of the system designer, a threshold greater than 2 cm can be used if desired. For example, if the pulse 14 has a period of 0.2 nanoseconds (ns) (i.e., $2\times10^{-10}$ sec), then the blind range is $\frac{1}{2}\times2\times10^{-10}$ s$\times3\times10^{10}$ cm/s=3 cm. That is, for a target 16 at a range of 3 cm from RADAR antenna 12, a 0.2 ns pulse would complete at exactly the time the reflection from beginning of the pulse 14 is returned to the RADAR antenna 12 as the reflected signal 18. The RADAR apparatus 12, 20, 22, 24 of the present disclosure detects the TOF or distance, d, of the object 16 through the full thickness of the portion of the patient support apparatus 10 through which pulse 14 and reflected signal 18 travel. Mattresses or pads used on patient support systems 10 are sometimes on the order of about 12 inches thick or more, for example.

The blind range is a term referring to the inability of the RADAR antenna to adequately receive a reflected signal 18 during transmission of the pulse 14. A pulse having a period of $6.25\times10^{-11}$ seconds per pulse has a blind range of 1.875 cm. Thus, to detect an object 16 at a range of 1.875 cm or more, the pulse period should be no longer than $6.25\times10^{-11}$ seconds. In some embodiments, driver circuitry 20 is configured as an ultra-wideband N-bit digitally tunable pulse generator that produces pulses typically as narrow as 0.55 ns (550 ps). While detecting immersion of the patient 16 to within about 2 cm to about 2.5 cm of bottoming out is possible according to this disclosure, in some embodiments, immersion of a patient to within about 5 cm to about 7 cm of bottoming out is sufficient. In such embodiments, the pulse period can be longer than the pulse periods just mentioned. Other systems, for example using a bi-static RADAR described in connection with FIG. 2 below, allow detection of the reflected signal 18 during the blind period.

Figure 16:
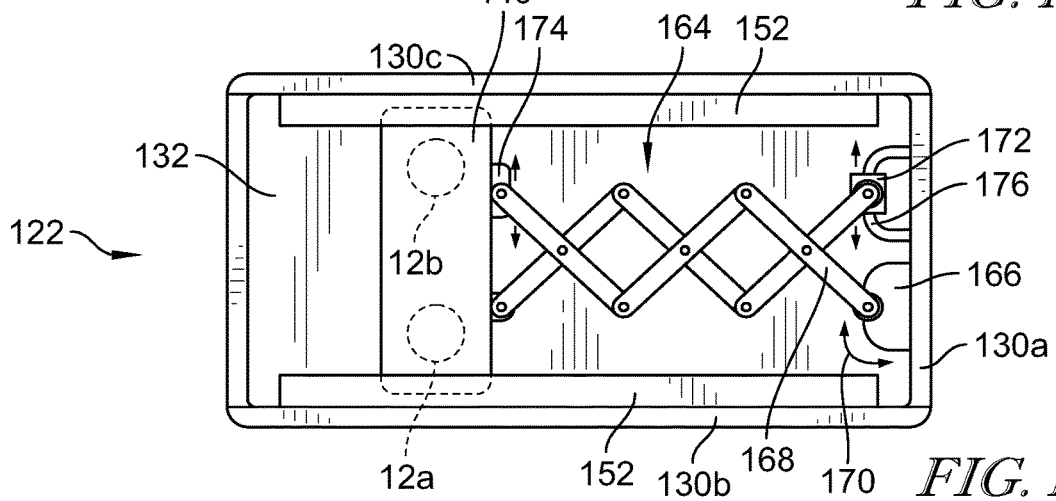
FIG. 16 is a bottom plan view of a deck section of the mattress support deck, similar to FIG. 15, showing a second alternative actuator for moving the movable plate, the second alternative actuator including a multi-stage scissors linkage interconnected between an end frame member of the deck section and the movable plate, a motor being mounted to the end frame member and operable to pivot a main link of the scissors linkage to extend and retract the scissors linkage to move the movable plate along the guides.
Figure 17:
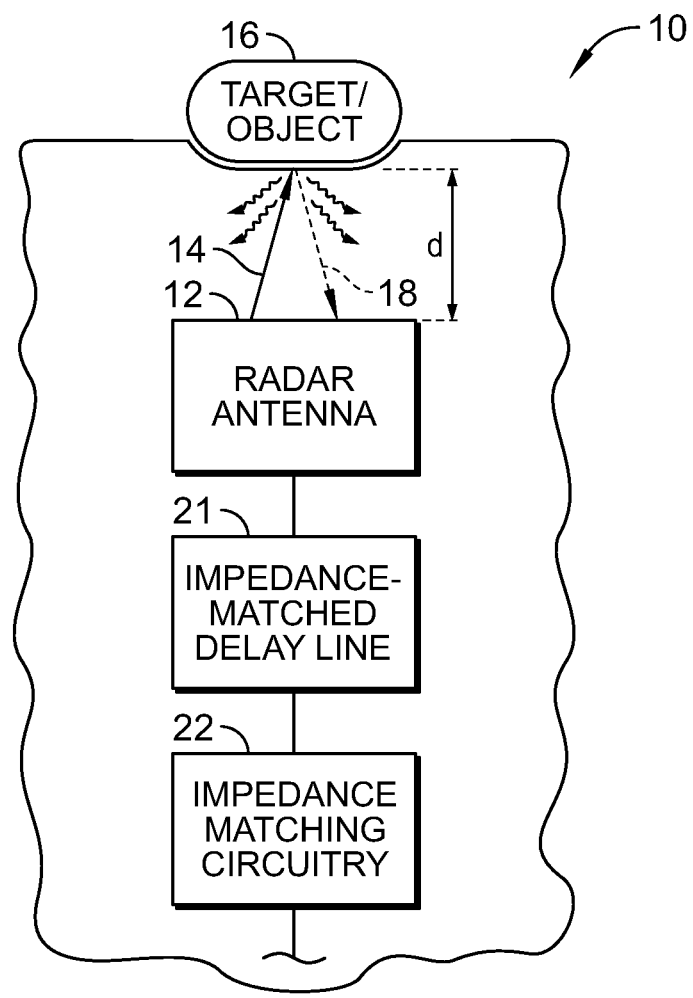
FIG. 17 is a block diagram showing a portion of a RADAR apparatus, similar to FIG. 1, but having an impedance-matched delay line interconnecting the RADAR antenna and the impedance matching circuitry.

Referring now to FIG. 17, the blind range of the RADAR system is modified, in some embodiments, by insertion of an impedance-matched delay line 21 between RADAR antenna 12 and impedance matching circuitry 22. Thus, the delay line 21 is coupled to the antenna 12 and to the impedance matching circuitry 22. FIG. 17 illustrates the relevant sub-portion of the patient support apparatus 10 from FIG. 1 to show the location of the delay line 21 in the RADAR system. Delays may be inserted at other locations to achieve that same effect. It should be appreciated that the other elements of the patient support apparatus 10, such as circuitry 20, 24, 26, etc. shown in FIG. 1 are also included in the RADAR system of FIG. 17 having delay line 21 for each antenna 12. Thus, the description above of the components of FIGS. 1-16, as well as variants thereof, is equally applicable to the RADAR system of FIG. 17 having delay line 21 for each antenna 12.

The delay line 21 creates the same effect as additional range between the respective antenna 12 and the target 16: it takes the pulse generated by driver circuitry 20 longer to reach the radar antenna 12 and similarly reflected signal 18 takes longer to return to the receiver circuitry 20. To illustrate this concept, consider the situation in which driver circuitry 20 (or a transceiver) emits a 1 nanosecond pulse 14, the start of that pulse will have travelled d=c×1 nanosecond=30 cm before the RADAR antenna 12 completes transmission of the pulse 14. If the range, d, to the target 16 is 15 cm or less, then the reflected signal 18 will return to the RADAR antenna 12 while the antenna 12 is still emitting the pulse 14.

Now consider the situation in which the antenna 12 is connected to the impedance matching circuitry 22, and therefore to the transceiver 20, by a length of RF transmission line, e.g., printed circuit board (PCB) microstrip, coaxial cable, a waveguide, or other type of delay line 21 known to those familiar in the art, that is 30 cm long. Assuming that the RF signal travels at the speed of light, c, in the transmission line, the leading edge of the pulse 14 reaches the antenna 12 as the trailing edge leaves the transmitter (e.g., RF driver portion) 20 after having traveled through the impedance matching circuitry 22 and delay line 21. The reflected signal 18 also takes an additional nanosecond to reach the receiver (e.g., RF receiver portion) 20 after having traveled through the delay line 21 and impedance matching circuitry 22. For an object 16 that is 3 cm away from the antenna 12, the pulse 18 reflects 1.1 nanoseconds after being emitted. By subtracting the known 1 nanosecond delay created by the length of the delay line 21, the processor circuitry 24 of the RADAR system determines that the reflection occurred 0.1 nanoseconds after the pulse 14 left the antenna 12. Multiplying by the speed of light, c, results in the actual range, d, being calculated as 3 cm.

Referring once again to FIG. 1, processor circuitry 24 is coupled to patient support system control circuitry 26 in the illustrative example. In some embodiments, each of circuitry 24, 26 include a microprocessor or microcontroller along with associated memory, power circuitry, input/output circuitry, clock or oscillator, etc. The microcontroller of circuitry 24 executes instructions to control the other portions of RADAR apparatus 12, 20, 22 and circuitry 26 executes instructions to control functions of patient support system 10. In other embodiments, circuitry 24 is included in circuitry 26. In such embodiments, a microprocessor or microcontroller of circuitry 26 executes instructions to control functions of the patient support system 10 and the RADAR apparatus 12, 20, 22. In such embodiments, circuitry 26 is considered to be the processor circuitry of the RADAR apparatus and the control circuitry of patient support system 10. Thus, the discussion above of various processing and calculations made by circuitry 20, 24, such as that regarding TOF and distance, d, determinations and regarding setting or adjusting bladder pressures, is performed by circuitry 26 in whole or in part, in some embodiments.

Circuitry 26 is coupled to a pneumatic system 28 of patient support system 10 as shown diagrammatically in FIG. 1. Pneumatic system 28 operates to control inflation of one or more air bladders 30 of patient support system 10. For example, if distance d or TOF is greater than a first threshold distance or TOF, respectively, then the pneumatic system 28 controls inflation by deflating one or more air bladders 30 so that the patient 16 immerses into the associated mattress or pad by a greater extent, thereby, reducing the distance d or TOF and lowering interface pressure between the patient 16 and the mattress or pad due to a greater surface area of contact between the patient 16 and the mattress or pad. If distance d or TOF is less than a second threshold distance or TOF, respectively, then the pneumatic system 28 controls inflation by inflating one or more air bladders 30 so that the risk of the patient 16 bottoming out is reduced due to increasing the distance d or TOF. Thus, in some embodiments, the pneumatic system 28 is operated by control circuitry 26 so that an amount of immersion of the patient 16 into a patient support surface is between the first threshold distance or TOF and the second threshold distance or TOF.

Pneumatic system 28 is shown diagrammatically in FIG. 1 and is intended to represent the various components that are used to inflate and deflate air bladders 30. Thus, pneumatic system 28 includes one or more air sources such as a blower, compressor, or pump; one or more valves such as solenoid valves, rotary valves, check valves, pressure relief valves; manifolds, manifold blocks; conduits such as tubes, hoses, passageways; pressure sensors; and the like.

Circuitry 26 is also coupled to one or more actuators 32 that are operable to move movable components 34 of patient support system 10. In some embodiments, actuators 32 include electromechanical actuators such as linear actuators, motorized jack screws, motors that operate linkage systems, and the like. In other embodiments, actuators 32 include hydraulic or pneumatic cylinders. Movable components 34 include sections of a mattress support deck in some embodiments. Such mattress support deck sections may include one or more of head, seat, thigh, and foot sections. Other movable components include table tops of imaging tables, surgical tables, examination table, or the like; chair frame sections, wheelchair frame sections; patient lift sections; and the like.

In the case of a patient bed having a head section of a mattress support deck that pivotably raises and lowers relative to a seat section, an amount of weight of a patient bearing downwardly in a seat region of a mattress supported by the seat section increase as the head section is raised. Thus, according to this disclosure, if the TOF or distance, d, reaches a lower threshold limit indicative of a risk that the patient may bottom out in the seat region of the mattress, the head section of the patient bed may be lowered automatically by control circuitry 26 or the raising movement of the head section may be suspended by control circuitry 26. In some embodiments, the head section may resume raising after the pneumatic system has had time to inflate one or more bladders 30 in the seat region of the mattress by a sufficient amount to eliminate the risk of the patient bottoming out if the head section were to be raised further. A message during the suspension in raising the head section may be displayed on a display screen of the patient bed in some embodiments to inform the user (e.g., a caregiver or patient pressing a head up button) that raising the head section is being paused until the seat section is further inflated to prevent bottoming out of the patient.

Still referring to FIG. 1, patient support system 10 includes a power interface 35 and a network interface 36 coupled to control circuitry 26. Power interface 35 is configured to couple with a connector 37 at one end of a power cord 39. An opposite end of the power cord 39 has a standard alternating current (AC) power plug 41 for connection to a standard AC power outlet. Network interface 36 includes, for example, a port for wired connection to a network 38 of healthcare facility and/or a transceiver for wireless communication with the network 38 via a wireless access point in some embodiments. Data from RADAR apparatus 12, 20, 22, 24 of patient support apparatus 10 is transmitted to at least one remote server 40 for storage and analysis. Server 40 may be a nurse call server of a nurse call system such as the HILL-ROM® NAVICARE® nurse call system, an electronic medical records (EMR) server of an EMR system, or some other server such as the WELCH ALLYN® CONNEX® server.

If the TOF or distance d indicates that the patient 16 is at risk of bottoming out, an alert message is transmitted from server 40 via network 38 to a caregiver or clinician notification device 42. Examples of clinician notification devices 42 according to this disclosure include handheld wireless communication devices such as smart phones, tablet computers, telephone handsets such as those available from ASCOM or Spectralink, for example, communication badges such as those available from Vocera, and pagers. Other types of clinician notification devices 42 include graphical audio stations that are mounted in patient rooms as part of a nurse call system and computer terminals that may be co-located with the clinician. Thus, one of servers 40 may be included in a real time locating system (RTLS) that tracks the locations of clinicians within a healthcare facility. The alert message is sent to the notification device 42 that is at the same location as the clinician assigned to the patient 16 who is at risk of bottoming out. The data regarding TOF and/or distance, d, may be stored in server 40 at periodic intervals (e.g., every 5 minutes, every 15 minutes, every hour) so that a patient's immersion history profile may be generated by server 40 and so that compliance reports can be generated by server 40 relating to whether or not the patient bottomed out on a mattress of the patient support system 10.

In some embodiments, server 40 stores demographic data relating to patients 16 that are supported on various patient support systems 10. Thus, server 40 aggregates the data received by the control circuitry 26 from the at least one RADAR system 12, 20, 22, 24 of various patient supports systems 10 and transmitted by the respective control circuitry 26 along with position data relating to the position of one or more movable components 34 of the respective patient support system 10. Other demographic data concerning each patient is received by server 40 from other sources, such as another server 40 such as an admission/discharge/transfer (ADT) server 40, in some embodiments. Bedsore data including data relating to clinical results of bedsores is also provided to server 40 for the various patients 16 on patient support systems 10. The demographic data relates to patient demographics and includes, for example, patient condition such as being of limited mobility, patient disease history, patient height, patient weight, and patient age. Older patients have thinner skin and less mobility than younger patients, for example.

According to this disclosure, data mining of the information stored in server 40 may be performed to discover correlations between the stored data (e.g., demographic data, bedsore data, TOF data, distance d data, etc.). Thus, factors leading to better patient outcomes (e.g., less bedsores) may be identified. For example, for a given mattress configuration, optimum ranges of patient immersion toward bottoming out may be identified. The optimum ranges are the ranges of TOF and/or distance, d, that result in the least amount of bedsore formation for patients, for example. These optimum ranges may vary by patient size, weight, and age and may vary from mattress to mattress.

Figure 2:
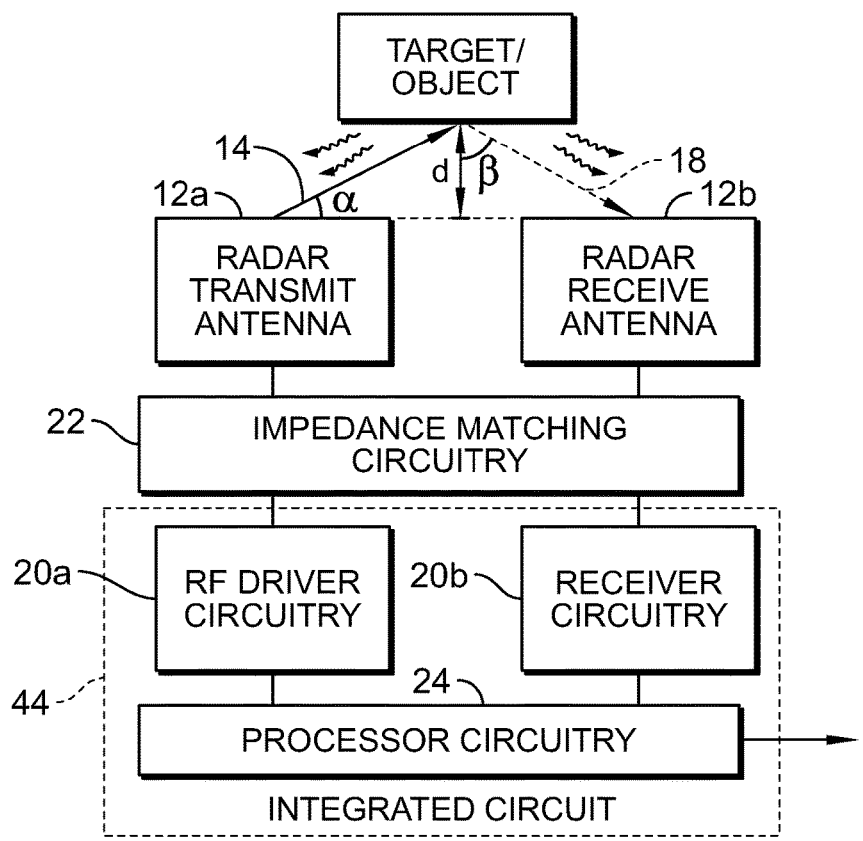
FIG. 2 is a block diagram showing an alternative embodiment of the RADAR apparatus of FIG. 1, the alternative embodiment RADAR apparatus having a RADAR transmit antenna and a RADAR receive antenna separate from the RADAR transmit antenna, impedance matching circuitry coupled to the RADAR transmit and receive antennae, RF driver circuitry and receiver circuitry coupled to the impedance matching circuitry, and processor circuitry coupled to the RF driver circuitry and receiver circuitry, the RF driver circuitry and the processor circuitry optionally packaged as an integrated circuit (in phantom)

Referring now to FIG. 2, an alternative embodiment of a RADAR apparatus includes a RADAR transmit antenna 12a and a RADAR receive antenna 12b that is separate from the RADAR transmit antenna 12a. Impedance matching circuitry 22 is coupled to the RADAR transmit and receive antennae 12a, 12b. The alternative RADAR system has RF driver circuitry 20a that is separate from receiver circuitry 20b. However, circuitry 20a and circuitry 20b are both coupled to the impedance matching circuitry 22. Furthermore, processor circuitry 24 is coupled to the RF driver circuitry 20a and receiver circuitry 20b. In some embodiments, the RF driver circuitry 20a, receiver circuitry 20b, and the processor circuitry 24 are packaged as an integrated circuit 44 as shown diagrammatically in FIG. 2 (in phantom). It should be understood that the one or more of the alternative RADAR apparatus 12a, 12b, 20a, 20b, 22, 24 of FIG. 2 can be substituted for one or more of the RADAR apparatus 12, 20, 22, 24 of the patient support system 10 of FIG. 1. Thus, the discussion above regarding FIG. 1 is equally applicable to RADAR apparatus 12a, 12b, 20a, 20b, 22, 24 of FIG. 2 except where noted below.

In FIG. 1, pulse 14 and reflected signal 18 are illustrated diagrammatically to be at an angle to each other for purposes of discussion and for ease of illustration. However, when a single antenna 12 is used as both the transmit antenna and the receive antenna (and considering the primary path), the transmitted pulse and reflected signal travel along basically the same path, such as vertically, in the illustrative arrangement of FIG. 1. However, in the FIG. 2 embodiment, the spacing between transmit antenna 12a and receive antenna 12b results in an angular path for pulse 14 from antenna 12a to the object 16 and then for reflected signal 18 from the object 16 to receive antenna 12b. In order to calculate distance, d, in the FIG. 2 arrangement, the angle of pulse 14 and/or reflected signal 18 should be accounted for to obtain an accurate measurement. This can be accomplished either by using angle $\alpha$ between the direction of pulse 14 and horizontal (really, the plane of antenna 12a, 12b which is illustratively horizontal) or by using angle $\beta$ between the direction of reflected signal 18 and vertical (really, the direction normal to the plane of antenna 12a, 12b which is illustratively vertical). The distance, d, can be calculated as either $d=(TOF \times c/2) \times sine(\alpha)$ or $d=(TOF \times c/2) \times cosine(\beta)$.

Once distance, d, is determined, it can be used as the control parameter by control circuitry 26 for adjusting inflation of bladders 30 and/or moving one or more movable components 34 of the patient support system 10 in the same manner as described above. It should also be noted that TOF can still be used as the control parameter with regard to adjusting inflation of bladders 30 and/or moving movable components 34 of patient support system 10 in the RADAR apparatus embodiment of FIG. 2 as long as the appropriate minimum and maximum TOF thresholds are selected corresponding to the minimum desired distance, d, toward bottoming out and the maximum distance, d, for desired interface pressure distribution of the patient 16 on the mattress or pad.

Figure 3:
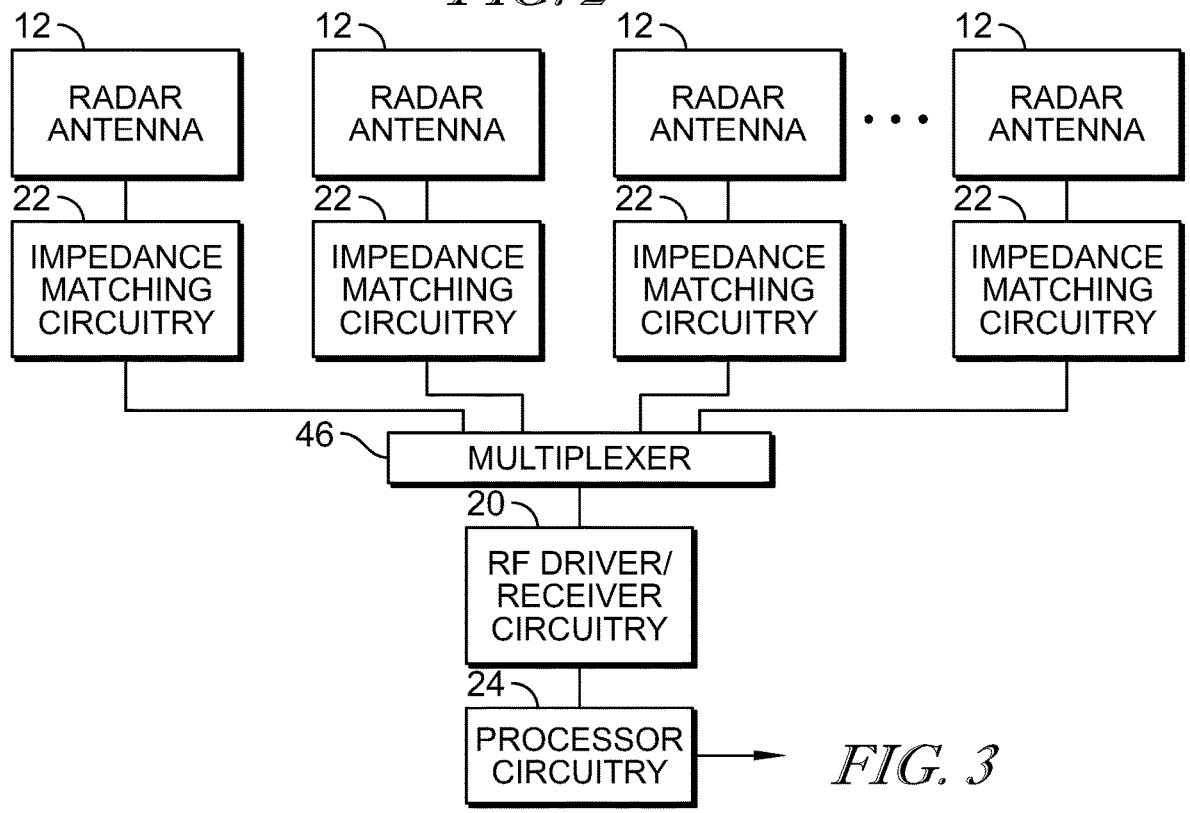
FIG. 3 is a block diagram showing a second alternative embodiment of the RADAR apparatus of FIG. 1, the second alternative embodiment RADAR apparatus having multiple RADAR antennae and multiple corresponding impedance matching circuitry and a multiplexer to select which of the RADAR antennae are active, the multiplexer being coupled to RF driver/receiver circuitry (aka RF transceiver circuitry) which is shared by the multiple RADAR antennae and processor circuitry which is coupled to the RF transceiver circuitry and which is shared by the multiple RADAR antennae.

Referring now to FIG. 3, another alternative embodiment of a RADAR apparatus includes a multiplexer 46 to connect RF driver/receiver circuitry 20 and processor circuitry 24 to selected ones of radar antennae 12 via corresponding impedance matching circuitry 22. Thus, unlike the RADAR apparatus embodiment of FIG. 1 in which each antenna 12 has its own circuitry 20, 24, the RADAR apparatus embodiment of FIG. 3 uses multiplexer 46 so that circuitry 20, 24 is shared among the RADAR antennae 12. Accordingly, the RADAR apparatus 12, 20, 22, 24, 46 of FIG. 3 is less costly and has less circuit components than the embodiment of FIG. 1.

Multiplexer 46 may be operated in any desired manner to cycle through the RADAR antennae 12 to select which one of RADAR antenna 12 is active for emission of pulse 14 and receipt of reflected signal 18 with the remaining antennae 12 being dormant. In further variants, each antenna 12 of the FIG. 3 embodiment is replaced with antennae 12a, 12b of FIG. 2 and/or circuitry 20 of the FIG. 3 is replaced with circuitry 20a, 20b of FIG. 2. It should be understood that the alternative RADAR apparatus 12, 20, 22, 24, 46 of FIG. 3, or its variants just mentioned, can be substituted for the RADAR apparatus 12, 20, 22, 24 of the patient support system 10 of FIG. 1. Thus, the discussion above regarding control of the patient support system 10 by circuitry 26 based on distance, d, or TOF in connection with FIG. 1 is equally applicable to RADAR apparatus 12, 20, 22, 24, 46 of FIG. 3 and its variants.

RADAR apparatus 12, 20, 22, 24 receives the power for operation from control circuitry 26 of patient support apparatus 10 in some embodiments. Circuitry 26 receives its power from power cord 39 that plugs into an AC power outlet in room of a healthcare facility, for example. Power interface 35 and/or circuitry 26 includes power isolation circuitry and power conversion circuitry to convert the 110-250 Volt, 50/60 Hertz standard AC power into the various voltage levels (e.g., 5 V DC, 24 V DC, 12 V DC) required to operate the various components of the patient support apparatus 10, including the RADAR apparatus 12, 20, 22, 24. In some embodiments, power interface 35 and/or control circuitry 26 includes one or more batteries that provide power to the various components of patient support apparatus 10, including the RADAR apparatus 12, 20, 22, 24 when the power cord 39 is unplugged from the AC power outlet. Other RADAR architectures known to those familiar with the art may be used.

In some embodiments it is contemplated that each antenna 12 is a planar antenna. Having a planar or flat antenna 12 permits use of the antenna 12 inside of a mattress or pad, as will be discussed below in connection with FIGS. 10A-10C, or just underneath a mattress or pad, as will be discussed below in connection with FIGS. 11A and 11B, without resulting in a large bump or protrusion which would potentially be felt by the patient 16 or interfere with the support capabilities of the mattress or pad. Examples of suitable planar antennae 12 are shown in FIGS. 4 and 5.

Figure 4:
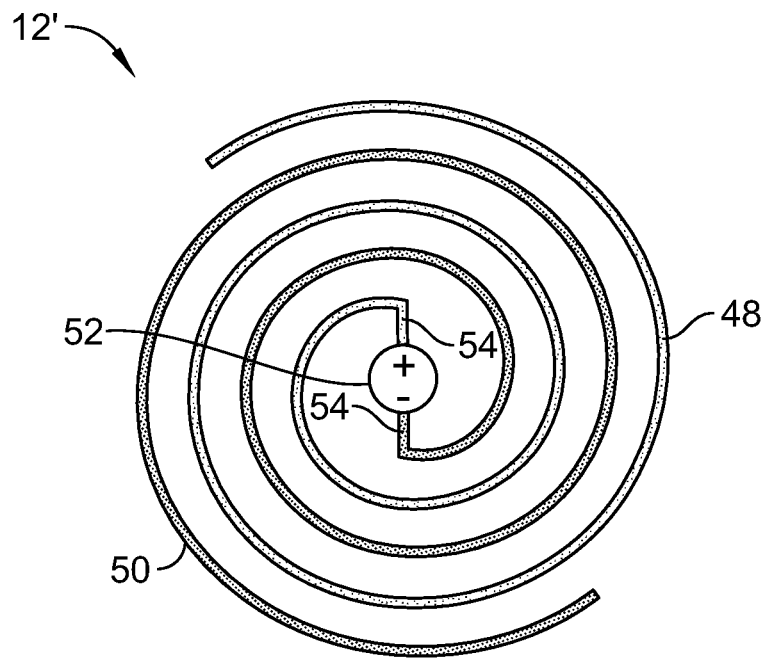
FIG. 4 is a top plan view of an Archimedean spiral antenna which is suitable for use in connection with the RADAR apparatus of the patient support system of FIG. 1.

Referring to FIG. 4, an Archimedean spiral antenna 12' is shown. Archimedean spiral antenna 12' may be used as any of antennae 12, 12a, 12b discussed above in connection with FIGS. 1-3. Antenna 12' includes a conductive first arm 48 that electrically couples to a positive terminal of a voltage feed 52 and a conductive second arm 50 that electrically couples to a negative terminal of the voltage feed 52. Voltage feed 52 is the interface between impedance matching circuitry 22 and antenna 12'. The geometry of arms 48, 50 is the same, although the arms 48, 50 are rotated 180 degrees with respect to each other, and is defined by the formula, $r = a \varphi$ in which r is the radius from the center of the spiral, a is coefficient and P is the angle from the starting point of the spiral. In the illustrative example, $a=0.1$. Also in the illustrative example, a short, straight, conductive segment 54 interconnects an inner end of each arm 48, 50 to the voltage feed 52.

Figure 5:
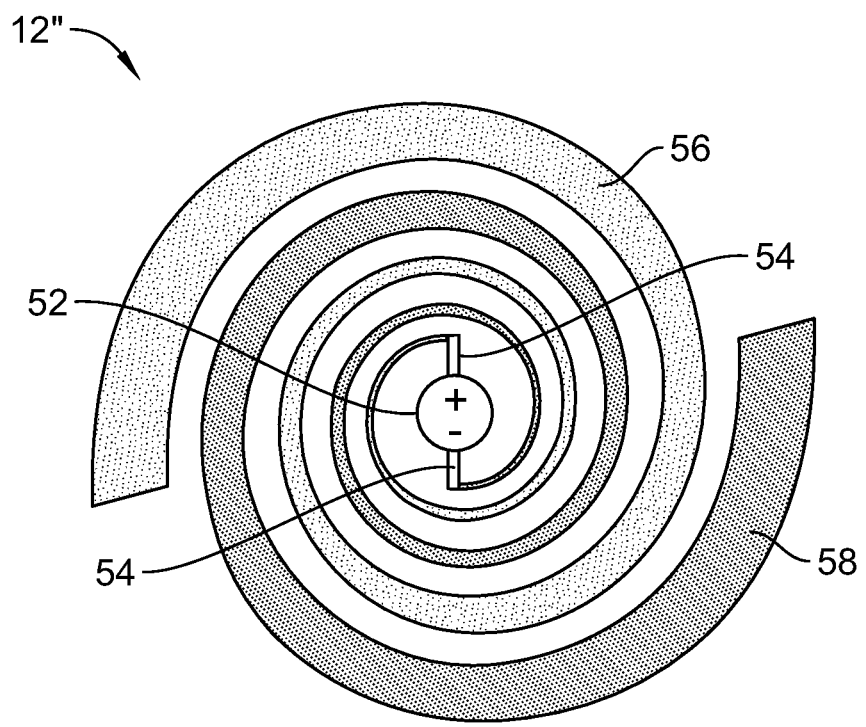
FIG. 5 is a top plan view of log-periodic spiral antenna which is suitable for use in connection with the RADAR apparatus of the patient support system of FIG. 1.

Referring to FIG. 5, a log-periodic spiral antenna 12" is shown. Log-periodic spiral antenna 12" may be used as any of antennae 12, 12a, 12b discussed above in connection with FIGS. 1-3. Antenna 12" includes a first conductive arm 56 that electrically couples to the positive terminal of voltage feed 52 and a conductive second arm 58 that electrically couples to the negative terminal of the voltage feed 52. Voltage feed 52 is the interface between impedance matching circuitry 22 and antenna 12". The geometry of arms 56, 58 is the same, although the arms 56, 58 are rotated 180 degrees with respect to each other, and is defined by the formula, $r = R_o e^{a\varphi}$ in which r is the radius from the center of the spiral, $R_o$ is a constant that dictates the initial radius of the spiral, a is coefficient that dictates the amount that each arm 56, 58 flares or grows as it turns, and $\varphi$ is the angle from the starting point of the spiral. A suitable value for a is 0.22.

In the illustrative example, short, straight, conductive segments 54 interconnect inner ends of each arm 46, 58 to the voltage feed 52.

The antenna beam from antenna 12', 12" is normal to the plane of the antenna 12', 12". Furthermore, the number of turns of arms 48, 50 of antenna 12' and the number turns of arms 56, 58 of antenna 12" may range from about H turn to about 3 turns at the option of the designer, with about 1% turns being a typical number for spiral antennae. Spiral antennae 12', 12" also have the benefit of exhibiting the antenna characteristic of circular polarization. Circular polarization is often used because it has a good ability to reject specular reflection components of multipath signals. Specular reflections in RADAR systems, such as those off of metallic surfaces, will have a circular polarization that is in the opposite polarity (rotating the opposite direction) compared to the incident signal (e.g., pulse 14) whereas the reflected signal 18 of interest will have the same polarity. Thus, by use of circular polarization, the signals with the opposite rotation direction from the pulse 14 are rejected by the antenna. That is, a right-hand (RH) circularly-polarized antenna cannot receive left-hand (LH) circularly polarized signals because reflections of a RH circularly polarized signal from a metal surface would be LH circularly polarized and rejected. Thus, by using spiral antennae 12', 12" the reflected signal 18 of interest is accepted with less noise from specular reflections of opposite polarity. Spiral antennae also have a large bandwidth and are suitable for operating over a wide range of frequencies as are required for ultra-wide band (UWB) RADAR systems.

Voltage feed 52 of impedance matching circuitry 22 of the present disclosure is configured as a balun in some embodiments. Thus, the voltage feed 52 is sometimes referred to herein as balun 52. A balun is a type of transformer that is used to convert an unbalanced signal to a balanced one or vice versa. Baluns isolate a transmission line and provide a balanced output. The term is derived by combining the words balanced and unbalanced. Use of a balun 52 with the antennae disclosed herein ensures that both arms of the spiral antenna (e.g., arms 48, 50 of antenna 12' and arms 56, 58 of antenna 12") have balanced currents. A broadband balun 52 should be use for a wide-band antenna.

Figure 6:
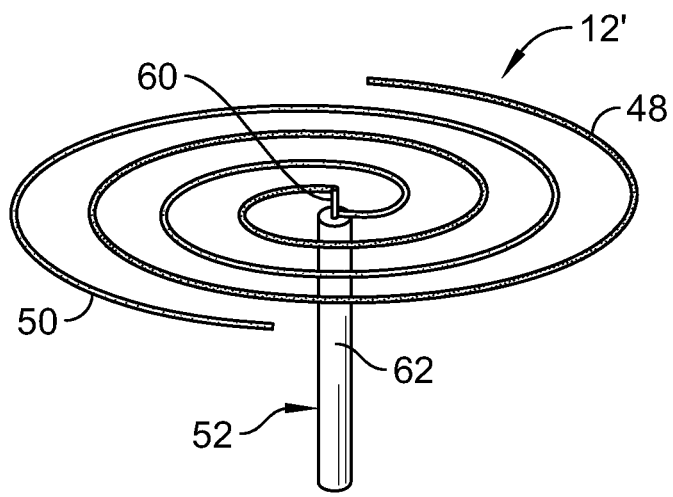
FIG. 6 is perspective view of an infinite balun, in the form of a coaxial cable, which is included in the impedance matching circuitry of FIG. 1 in some embodiments, coupled to a spiral antenna, the coaxial cable having its center conductor coupled to a first arm of a pair of arms of the spiral antenna, and the coaxial able having its outer conductor coupled to a second arm of the pair of arms of the spiral antenna.

Referring now to FIG. 6, balun 52 is configured as an infinite balun, which in the illustrative example, includes a coaxial cable that is electrically coupled to spiral antenna 12'. The coaxial cable has its center conductor 60 coupled to first arm 48 of antenna 12' and has its outer conductor or ground shielding coupled to second arm 50 of antenna 12'. Outer cladding 62 of the coaxial cable surrounds the ground shielding and thus, the ground shielding cannot be seen in FIG. 6. However, coaxial cables have well-known structures.

Figure 7:
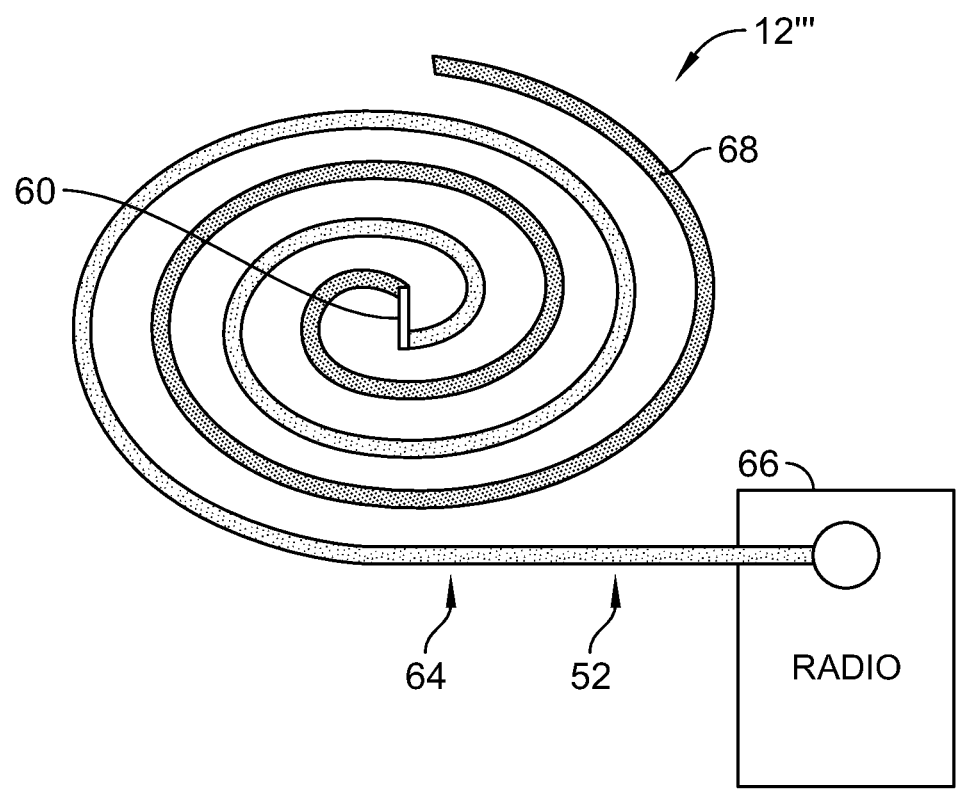
FIG. 7 is a top plan view of a second embodiment of an infinite balun showing a coaxial cable extending from a radio (e.g., RF driver/receiver circuitry of FIG. 1) and spiraled to form a first arm of a pair of arms of a spiral antenna, the coaxial cable having its center conductor coupled to a second arm of the pair of arms of the spiral antenna, the coaxial cable of the second embodiment serving as a portion of the RADAR antenna and a portion of the impedance matching circuitry of FIG. 1.

Referring now to FIG. 7, a second embodiment of an infinite balun is shown. In the second embodiment, a coaxial cable 64 extends from a radio 66 (e.g., RF driver/receiver circuitry 20 of FIG. 1) and is spiraled to form a first arm of a spiral antenna 12'''. In particular, the outer conductor or ground shielding of coaxial cable 64 is used as the first arm of antenna 12'''. Antenna 12''' includes a conductive second arm 68 as well. Antenna 12''' may be used as any of antennae 12, 12a, 12b discussed above in connection with FIGS. 1-3. The coaxial cable 64 of the spiral antenna 12''' serves as a portion of the RADAR antenna 12''' and as a portion of the impedance matching circuitry 22. Thus, coaxial cable 64 and balun 52 and one of the conductive arms of antenna 12''' are one in the same in the embodiment of FIG. 7.

Figure 8:
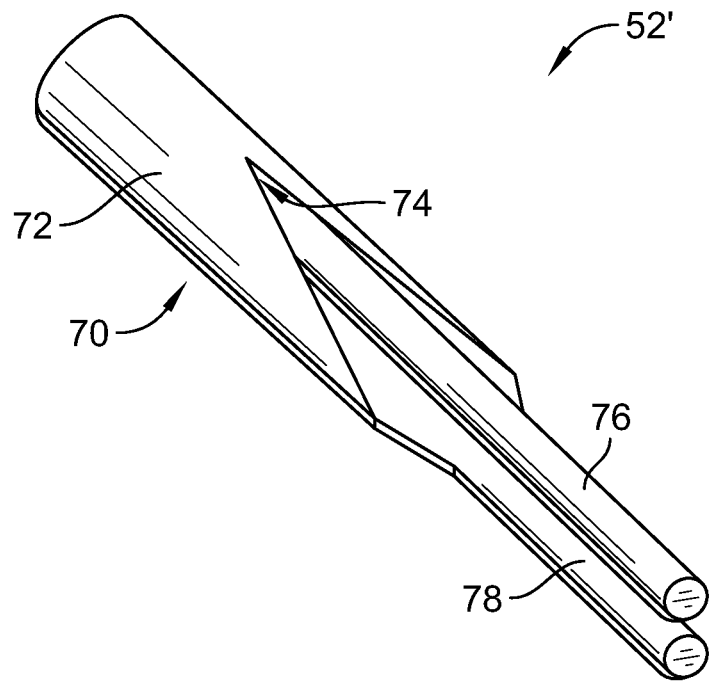
FIG. 8 is a perspective view of a portion of a tapered balun, in the form of a coaxial cable, which is included in the impedance matching circuitry of FIG. 1 in some embodiments, showing an outer conductor of the coaxial having a tapered notch with an end region of the outer conductor formed into a transmission line that is balanced with a center conductor of the coaxial cable.
Figure 9:
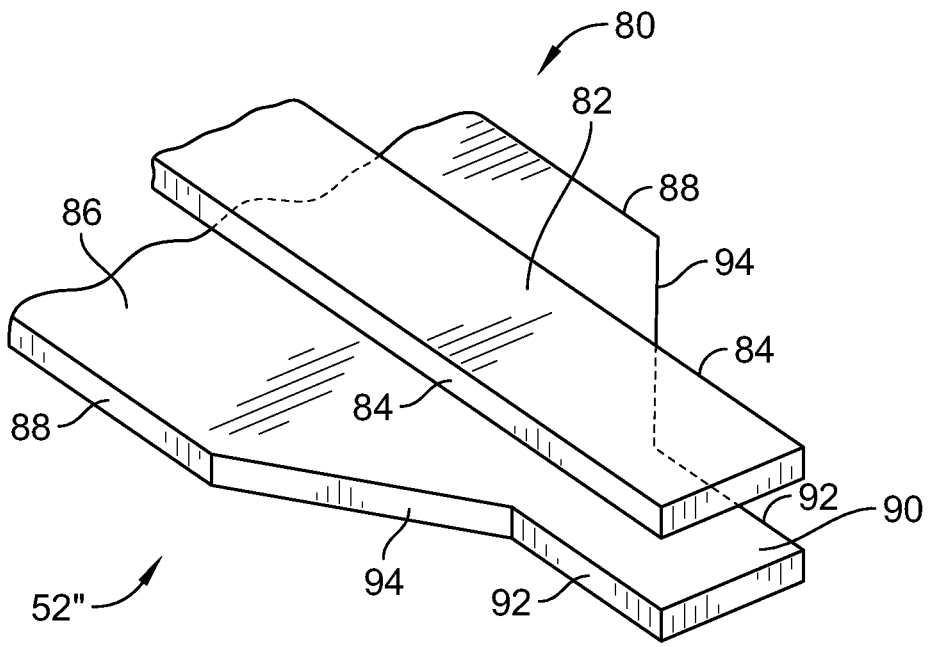
FIG. 9 is perspective view of another embodiment of a portion of a tapered balun, in the form of a microstrip transmission line, which is included in the impedance matching circuitry of FIG. 1 in some embodiments, showing a top strip of the tapered balun having uniform width along its length and a bottom strip having a wide portion that tapers down to an end portion having a substantially equivalent width as the top strip so as to form a balanced transmission line at the end portion of the tapered balun.

Optionally, a tapered balun rather than an infinite balun 52 may be used in impedance matching circuitry 22 as a voltage feed to the antennae 12, 12a, 12b, 12', 12", 12''' disclosed herein. A tapered balun gradually changes shape from an unbalanced transmission line to a balanced transmission line. One type of tapered balun 52' is shown in FIG. 8 and another type of tapered balun 52" is shown in FIG. 9. In FIG. 8, a portion of a coaxial cable 70 has its outer conductor 72 provided with a V-shaped notch 74 to permit the outer conductor 74 to be peeled away from a center conductor 76 so that an end region of the peeled away material can be reshaped into a conductor 78 having a shape that is substantially the same as the center conductor 76. Conductors 76, 78 are transmission lines having substantially equivalent shapes at the end of coaxial cable 70 and these transmission lines 76, 78 provide the positive and negative terminals for electrically coupling to the associated antenna such as antenna 12'. The geometry of the taper formed by notch 74 should be gradual so as to extend over several wavelengths of the expected pulse 14.

Referring now to FIG. 9, tapered balun 52" is formed in a microstrip transmission line 80. Transmission line 80 has a top strip 82 of uniform width between its opposite elongated edges 84. Transmission line 80 also has a bottom strip 86 which serves as a ground plane and which has a wide portion defined between its elongated opposite edges 88. Strip 86 tapers down to an end portion 90 having a substantially equivalent width between edges 92 as the width of top strip 82 between edges 84. Strip 86 has tapered edges 94 that transition from respective edges 88 to corresponding edges 92. Thus, end portion 90 of strip 86 has substantially the same shape as the overlying portion of strip 82. Accordingly, a balanced transmission line is provided at the end portion of the tapered balun 52". The taper of edges 94 should be gradual so as to extend over several wavelengths of the expected pulse 14. Strip 82 serves the positive terminal and provides the RF feed to one of the arms of the associated antenna, such as antenna 12', and strip 86 serves as the negative terminal which couples to the other arm of the associated antenna.

In the discussion of FIGS. 10A-16 that follows, reference is made simply to antenna 12 or antennae 12. However, each antenna embodiment disclosed herein (e.g., antenna 12, 12a, 12b, 12', 12", 12''') is contemplated as being a suitable antenna for use in the structures shown in FIGS. 10A-16. Also, the discussion that follows refers to various types of "mattresses." However, the discussion is equally applicable to mattress overlays, surgical pads, chair cushions or pads, and the like.

Referring now to FIG. 10A, a cross sectional view of a portion of an air mattress or support pad 100a is shown. Air mattress 100a supports the patient 16 thereon and includes a plurality of air bladders 30. In particular, with regard to the portion of mattress 100a shown in FIG. 10A, portions of air bladders 30a, 30b, 30c can be seen. Bladders 30a, 30b, 30c each include a layer of flexible material 31 that is substantially air impermeable and configured to form an enclosure to contain a volume of pressurized air therein. Mattress 100a includes a base foam layer 102 underlying bladders 30a-c. Mattress 100a also includes an outer ticking 104 including a top ticking layer 106 and a bottom ticking layer 108. Mattress 100a is supported by a frame 110 of patient support system 10. Mattress also includes a fire sock (not shown) which surrounds base foam layer 102, bladders 30a-c, any other bladders 30 of mattress 100a, and any other components of mattress 100a inside of the ticking 104, as is well known in the art. The patient support elements or components inside of the ticking 104 of mattress 100a, such as bladders 30a-c and base foam layer 102 in the FIG. 10A example, are considered to be the core of mattress 100a.

In the embodiment of FIG. 10A, RADAR antenna 12 is located inside of mattress 100a and is sandwiched between bottom ticking layer 108 and base foam layer 102. In the illustrative example, base foam layer 102 conforms around RADAR antenna 12. It should be appreciated that additional RADAR antennae 12 are sandwiched between bottom ticking layer 108 and base foam layer 102 at other locations throughout mattress 100a in some embodiments. The locations of RADAR antenna 12 within mattress 100a is at the discretion of the mattress designer. Each antenna 12 is operated to emit pulse 14 and receive reflected signal 18 as has been described above to determine TOF and, in some embodiments, distance d which is dictated by an amount of immersion of the patient 16 into mattress 100a in the region above antenna 12. It should be appreciated that conductors of the antenna feed 52 (or antenna feed 52', 52" as the case may be) are routed, at least in part, within the interior region of the mattress 100a.

Optionally, in some embodiments, a RADAR reflective coating 112 is provided on an inner surface of the top portion of material 31 of bladder 30a. In such embodiments, the RADAR reflective coating becomes the target or object which reflects pulse 14 as the reflected signal 18 and therefore, it is the TOF and/or distance, d, between RADAR antenna 12 and the RADAR reflective coating 112 which is determined or calculated. However, using the reflective coating 112 as the object or target still permits a determination to be made regarding the patient's risk of bottom out so that corrective action can be taken by circuitry 26 of patient support system 10 to mitigate the risk as discussed above.

Referring now to FIG. 10B, a cross sectional view of a portion of an air mattress or support pad 100b similar to the one of FIG. 10A is shown. Thus, the same reference numbers are used in FIGS. 10A and 10B to denote like components. Furthermore, the description of above of the components of mattress 100a of FIG. 10A is equally applicable to the like components of mattress 100b of FIG. 10B. The primary difference between mattress 100a and mattress 100b is that base foam layer 102 is omitted in mattress 100b. Also, in the mattress 100b of FIG. 10B, the lower portion of material 31 of bladder 30a conforms around antenna 12 which is sandwiched between the bottom ticking layer 108 and the lower portion of material 31 of bladder 30a.

Many mattresses have a base foam layer like layer 102 of mattress 100a of FIG. 10A to provide some cushioning for the patient 16 in the event of a bottoming out situation (e.g., the top portion of material 31 of bladder 30a is deflected all the way down under the weight of patient 16 to contact the bottom portion of material 31 of bladder 30a). However, because RADAR antenna 12 and the associate circuitry 20, 22, 24 of the RADAR apparatus provides an output to control circuitry 26 of the patient support apparatus 10 which, in appropriate circumstances, signals pneumatic system 28 to further inflate one or more bladders 30 and/or to signal one or more actuators 32 to move one or more associated movable components 34 so as to prevent the bottoming out condition, it is possible to eliminate base foam layer 102 from mattress 100a as shown in the mattress 100b embodiment of FIG. 10B.

Because base foam layer 102 is eliminated in mattress 100b of FIG. 10B, mattress thickness in the vertical dimension is less than the mattress 100a of FIG. 10A which has base foam layer 102. In other words, the thickness of mattress 100*b* is reduced by the amount of thickness of base foam layer 102 of mattress 100*a* which can be on the order of about 1 inch to about 3 inches or more in some mattresses. Having a "thinner" mattress 100*b* as compared to mattress 100*a* results in other design advantages to the frame 110 of patient support system 10. For example, in the embodiments in which patient support system 10 is a patient bed having frame 110 equipped with one or more siderails that each move between a raised position to block patient egress from the mattress 100*b* and a lowered position to permit patient egress, a vertical height of the one or more siderails of the patient bed 10 does not need to be as large with a thinner mattress. When such reduced height siderails are in the lowered positions, an upper frame portion of frame 110 can be lowered relative to a base frame portion of frame 110 (or relative to the underlying floor) to a lowermost position, sometimes referred to as a low/low position in the art, that places the patient 16 closer to the floor as compared to beds 10 having mattresses 100*a* with base foam layers 102 while still maintaining a sufficient gap between a bottom of the siderail and the floor to meet governmental and hospital regulations.

Referring now to FIG. 10C, a cross sectional view of another embodiment of a mattress or pad 100*c* is shown. Portions of mattress 100*c* that are substantially the same as like portions of mattress 100*a* are denoted by like reference numbers and the description above is equally applicable. Thus, the illustrative RADAR antenna 12 in FIG. 10C is sandwiched between the bottom ticking layer 108 and base foam layer 102 which conforms around RADAR antenna 12. One of the noticeable differences between mattress 100*c* of FIG. 10C and mattress 100*a* of FIG. 10A is that instead of the single layer of bladders 30, including illustrative bladders 30*a*-*c* of mattress 100*a*, mattress 100*c* has multiple layers of bladders 30. In particular, mattress 100*c* has a lower layer of bladders 30 above base foam layer 102 and an upper layer of bladders 30 above the lower layer of bladders. In FIG. 10C, portions of bladders 30*d*, 30*e*, 30*f* can be seen in the lower layer and portions of bladders 30*g*, 30*h*, 30*i*, 30*j*, 30*k* can be in the upper layer. Mattress 100*c* is configured so that three bladders 30 of the upper layer are situated above each bladder 30 of the lower layer. For example, bladders 30*g*, 30*h*, 30*i* of the upper air bladder layer of mattress 100*c* are situated over bladder 30*d* of the lower air bladder layer of mattress 100*c*.

Another difference between mattress 100*a* of FIG. 10A and mattress 100*c* of FIG. 10C is that mattress 100*c* has a microclimate management (MCM) layer 114 above the upper layer of bladders 30, such as bladder 30*g*-*k*, portions of which can be seen in FIG. 10C. In the illustrative example, upper ticking layer 106 is included as one of the components of MCM layer 114. MCM layer 114 also includes a bottom sheet or layer 116 and a three-dimensional (3D) engineered material layer 118 situated between layers 106, 116. The 3D engineered material 118 comprises an air permeable material which allows a stream of air to flow therethrough to wick moisture away from the patient 16 through upper ticking layer 106. Examples of suitable 3D engineered material includes, but is not limited to, fiber networks made from textile fabrics such as is shown and described in U.S. Pat. Nos. 5,731,062 and 5,454,142 owned by Hoechst Celanese Corporation, Somerville, N.J. and marketed as SPACENET® material. Other examples of suitable 3D engineered material includes Model No. 5875, 5886, 5898, and 5882 materials available from Muller Textile of Troy, Michigan and a molded thermoplastic spacer matrix material available from Akzo Nobel of Amsterdam, Netherlands. Thus, the term "three-dimensional (3D) engineered material" is meant to include any of these types of materials and similar materials.

RADAR antenna 12 of mattress 100*c* shown in FIG. 10C emits pulse 14 and receives reflected signal 18 through all of the illustrative components of mattress 100*c* that are situated between RADAR antenna 12 and the patient 16. Thus, the pulse 14 and reflected signal travel through foam base layer 102, one or more of bladders 30*d*-*f* of the lower bladder layer, one or more of bladders 30*g*-*k* of the upper bladder layer, MCM layer 114, and any other components of mattress 100*c* (e.g., a fire sock) included in mattress 100*c* and situated between RADAR antenna 12 and the patient 16.

As should be apparent from the mattress examples shown in FIGS. 10A-10C, RADAR apparatus 12, 20, 22, 24 can be used with mattresses or pads of all types regardless of the simplicity or complexity of the mattress design. In the examples of mattresses 100*a*-*c* of FIGS. 10A-10C, one or more RADAR antenna 12 are located inside of the respective mattress 100*a*-*c*. While RADAR antennae 12 are placed just above bottom ticking layer 108 in the illustrative examples of mattresses 100*a*-*c*, it is within the scope of this disclosure for RADAR antennae 12 to be placed elsewhere within the respective mattress 100*a*-*c*, such as on top of base foam layer 102 or inside of one or more of the bladders 30. However, it is preferable to place the RADAR antennae 12 close to the bottom of the mattress 100*a*-*c*, in the manner illustrated, so that the blind range of the RADAR apparatus 12, 20, 22, 24 is as close to the bottom of the mattress 100*a*-*c* as possible. RADAR antenna 12 may be secured in place within mattress 100*a*-*c* with adhesive, adhesive tape, hook-and-loop fasteners such as VELCRO® material, and the like. In some embodiments, additional material may be attached to an inner surface of bottom layer of ticking 108, such as by RF or sonic welding or by stitching, for example, to provide pockets which receive RADAR antennae 12.

Figure 11A:
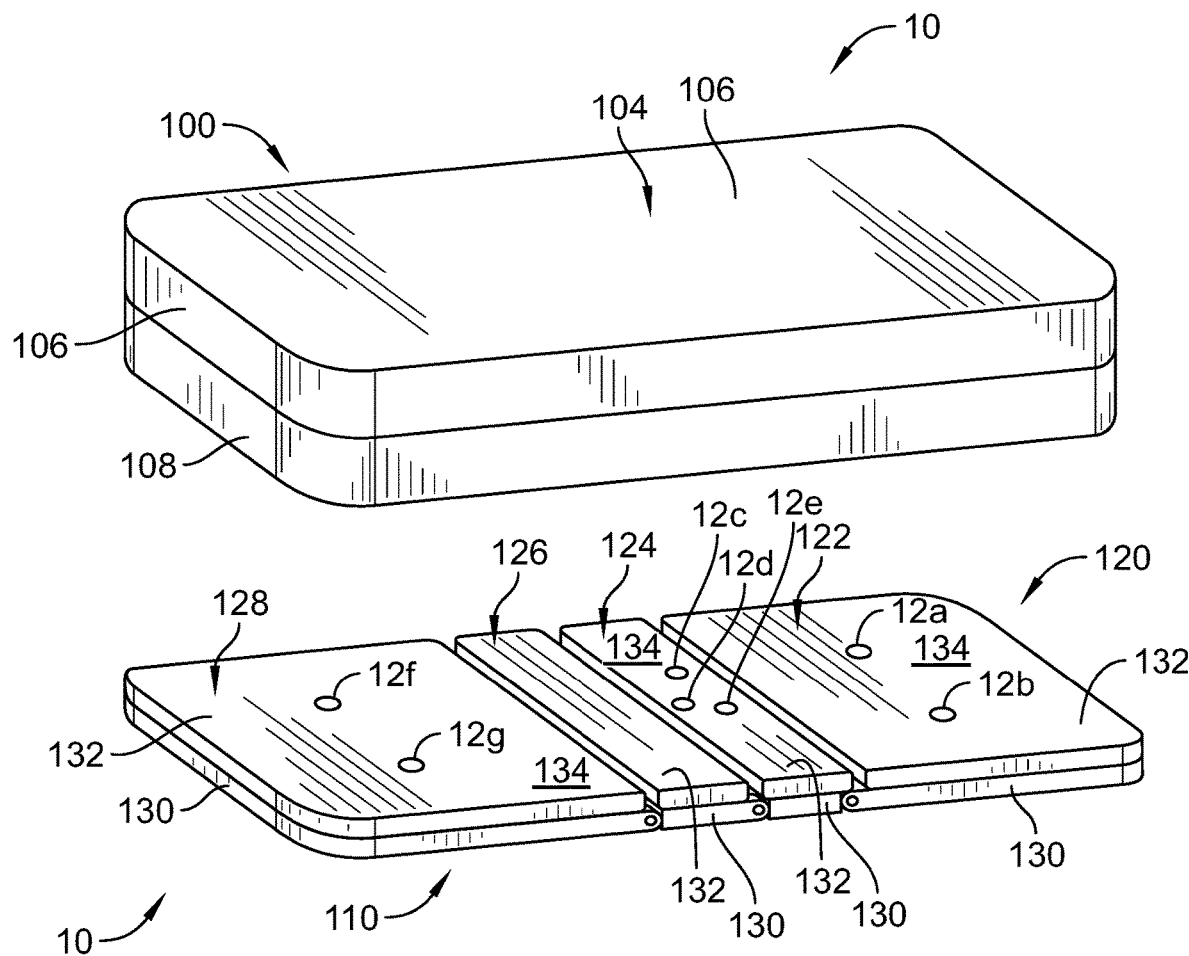
FIG. 11A is an exploded view of a portion of a patient support apparatus showing a mattress and an articulated mattress support deck of a frame of the patient support apparatus spaced downwardly from the mattress, an upper surface of a head section of the mattress support deck having two RADAR antennae coupled thereto, an upper surface of a seat section of the mattress support deck having three RADAR antennae coupled thereto, and an upper surface of a foot section of the mattress support deck having two RADAR antennae coupled thereto.

Referring now to FIG. 11A, a mattress 100 is exploded away from and an articulated mattress support deck 120 of frame 110 of the patient support apparatus 10. Deck 120 is illustrated in a simplified manner in FIG. 11A but is generally representative of those used on patient beds, stretchers, and surgical tables. Deck 120 includes a head or back section 122, a seat section 124, a thigh section 126, and a foot section 128. Head section 122 is pivotably coupled to a head end of seat section 124 and thigh section 126 is pivotably coupled to a foot end of seat section 124. Foot section 128 is pivotably coupled to a foot end of thigh section 126. In some patient beds, seat section 124 is affixed to an upper frame with sections 122, 126, 128 being movable, such as with the use of actuators 32, relative to seat section 124. Thus, sections 122, 126, 128 are articulated to various positions to support the mattress 100, and therefore, the patient 16 supported by mattress 100, in various positions.

Each of illustrative sections 122, 124, 126, 128 includes a framework 130, typically made of a metal material such as steel, and a support panel 132 that is situated atop the respective framework 130. Support panels are made of radiolucent materials such as a molded plastic material or carbon fiber or fiberglass or the like, although, it is within the scope of this disclosure for panels 132 to be made from a metal material if desired. Each panel 132 has an upper surface 134. In the illustrative example, RADAR antennae 12*a*, 12*b*, 12*c*, 12*d*, 12*e*, 12*f*, 12*g* are coupled to upper surfaces 134 of panels 132. Specifically, RADAR antennae 12*a*, 12*b* are coupled to upper surface 134 of panel 132 of head section 122; RADAR antennae 12*c*, 12*d*, 12*e* are coupled to upper surface 134 of panel 132 of seat section 124; and RADAR antennae 12*f*, 12*g* are coupled to upper surface 134 of panel 132 of foot section 128.

The location of RADAR antennae 12*a-g* on deck 120 generally coincide with locations at which bony prominences of the patient 16 would be expected when the patient 16 is lying in a supine position on mattress 100. Thus, RADAR antennae 12*a*, 12*b* are situated on head section 122 beneath the general locations where the right and left scapula of the patient 16 would be expected to lie on mattress 100. RADAR antennae 12*c*, 12*d*, 12*e* are situated on seat section 124 beneath the pelvic or sacral region of the patient 16. In particular, RADAR antennae 12*c*, 12*e* are situated on seat section 124 beneath the general locations where the patient's right and left iliac tuberosity would be expected to lie on mattress 100 and RADAR antennae 12*d* is situated on seat section 124 beneath the general location where the patient's coccyx would be expected to lie on mattress 100. Finally, RADAR antennae 12*f*, 12*g* are situated on foot section 128 beneath the general locations where the patient's right and left heels would be expected to lie on mattress 100.

It is within the scope of this disclosure to provide more RADAR antennae 12 on deck 120 than is shown in FIG. 11A. For example, in some embodiments, an additional RADAR antenna 12 is provided on head section 122 beneath the patient's head, but typically a pillow is placed under the patient's head and provides additional cushioning such that pressure ulcers are less likely on the patient's head than in the region of the patient's scapulae. One or more RADAR antennae 12 may be included on thigh section 126 as well, although, the thighs of patients typically are not susceptible to pressure ulcers. It is also within the scope of this disclosure to provide less RADAR antennae on deck 120 than is shown in FIG. 11A. For example, RADAR antennae 12*d* may be omitted in some embodiments. It should be appreciated that a respective antenna feed 52 is routed to each of RADAR antennae 12*a-g*, such as extending upwardly through respective holes (not shown) provided in panels 132 beneath antennae 12*a-g* or by being routed along upper surfaces 134 of panels 132 to the respective antennae 12*a-g*.

Figure 11B:
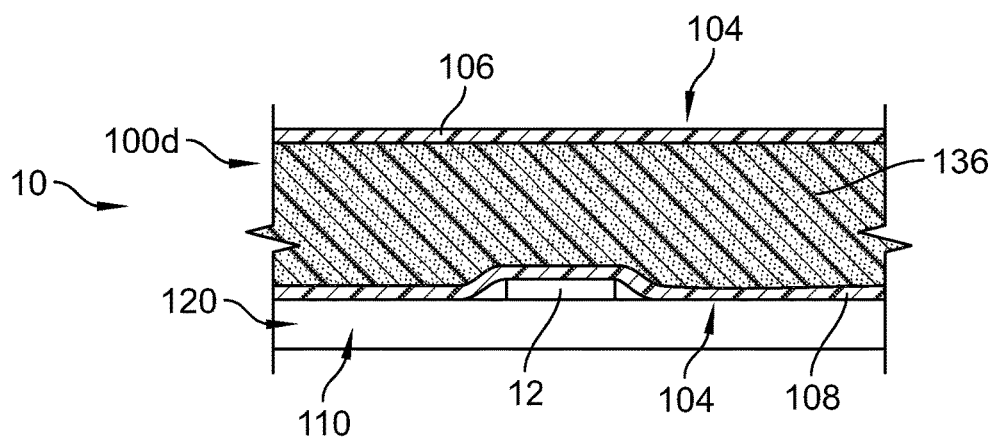
FIG. 11B is a cross sectional view of a foam mattress showing that the RADAR antenna is situated between a bottom ticking layer of the foam mattress and a frame of a patient support apparatus.

In some embodiments, RADAR antennae 12*a-g* protrude upwardly by a slight amount from upper surfaces 134 of panels 132 (e.g., see FIG. 11B). In other embodiments, panels 132 of deck 120 are provided with recesses or pockets in which RADAR antennae 12*a-g* are situated so that upper surfaces of the antennae 12*a-g*, or housings that may contain antennae 12*a-g*, are substantially flush or coplanar with surfaces 134 of panels 132. The present disclosure contemplates various types of fasteners that may be used to couple RADAR antennae 12*a-g* to deck 120. For example, adhesive such as glue or adhesive tape may be used in some embodiments. Hook-and-loop fasteners such as VELCRO® material may be used in some embodiments. In embodiments in which RADAR antennae 12*a-g* include housings, screws may be used to attach antennae 12*a-g* to panels 132 of deck 120. Snaps and clips are other examples of a suitable fastener for coupling RADAR antennae 12*a-g* to deck 120.

By providing RADAR antennae 12*a-g* on deck 120, rather than inside of mattress 100, the RADAR apparatus 12, 20, 22, 24 of the associated patient support system 10 may be used with any type of mattress placed on deck 120 to determine whether the patient is at risk of bottoming out on the particular mattress. In some embodiments, the patient support system 10 includes a user interface, such as a graphical user interface (GUI), which is used to select the type of mattress being supported on deck 120. For example, the GUI of system 10 may be used to indicate that one of mattresses 100*a-c* described above is the particular type of mattress supported on deck 120. Control circuitry 26 then may send information to processor circuitry 24 indicating the type of mattress on deck 120.

Different types of mattresses will have different impedances depending upon their particular constructions. According to this disclosure, the impedance of impedance matching circuitry 22 is adjusted to match the environment through which pulse 14 and reflected signal 18 travel. Thus, circuitry 26 and/or circuitry 24 includes information regarding the impedances of different mattress types and the impedance matching circuitry 22 is adjusted to match that of the particular mattress being used on deck 120. In this regard, switches such as transistors or microswitches may be turned on and off to select respective impedance elements (e.g., resistors, capacitors, inductors) for inclusion in the impedance matching circuitry 22 or exclusion from the impedance matching circuitry 22.

Alternatively or additionally, an impedance element may be dynamically adjusted to change the impedance of circuitry 22. For example, a rotary potentiometer or rheostat may be adjusted, such as with a small motor, to change its resistance. Similarly, an adjustable capacitor may have the spacing between its plates adjusted or the surface area of overlap adjusted in the case of a rotary variable capacitor to change its capacitance. A variable inductor in which a magnetic core is adjusted within a coil of wire to change its inductance is also contemplated. Furthermore, different zones of a mattress may have different impedances depending upon the construction of the various zones. Thus, impedance matching circuitry 22 for each RADAR antenna 12*a-g* on deck 120 may be different depending upon the construction of the portion of the mattress located above the particular RADAR antennae 12*a-g*.

Referring now to FIG. 11B, a cross sectional view of a foam mattress 100*d* is shown. Foam mattress 100*d* is filled with one or more foam layers 136 within ticking 104 between upper ticking layer 106 and bottom ticking layer 108. In the illustrative embodiment, one layer 136 of foam serves as the core of mattress 100*d* but in other embodiments, two or more layers of foam may be provided to serve as the core within ticking 104. Also in the illustrative example of FIG. 11B, RADAR antenna 12 is located on deck 120 of frame 110 of the patient support system 10 beneath the bottom layer of ticking 108 which, together with a portion of foam layer 136, conforms around RADAR antenna 12.

Even though there are no air bladders in mattress 100*d* to be adjusted, there is still a benefit in using RADAR apparatus 12, 20, 22, 24 to monitor the immersion of the patient 16 into mattress 100*d* by monitoring or determining the TOF or the distance, d. Over time, the support characteristics of foam are known to degrade. Depending upon the type of foam, mattress 100*d* may get harder over time, due to oxidation for example, or mattress 100*d* may get softer, due to fracturing of the cellular material of the foam. Also, some foam materials, such as viscoelastic foam, may become permanently compressed or deformed, thereby losing its cushioning capabilities and becoming harder. Thus, depending upon the weight of the patient 16 as measured by weight scale of the patient support system 10, the amount of immersion into mattress 100*d* may be expected to be between a maximum and minimum threshold.

The minimum immersion threshold corresponds to a maximum threshold for TOF and/or distance, d, and the maximum immersion threshold corresponding to a minimum TOF and/or distance, d. Some or all of these maximum and minimum thresholds may be stored in memory of circuitry 26 or circuitry 24. If RADAR system 12, 20, 22, 24 used with a foam mattress, such as mattress 100d, indicates that TOF or distance, d, is greater than the maximum threshold for the patient 16 of a given weight, then this is indicative that the foam layer 136 in mattress 100d has degraded and become too hard. On the other hand, if RADAR system 12, 20, 22, 24 used with a foam mattress, such as mattress 100d, indicates that TOF or distance, d, is smaller than the minimum threshold for the patient 16 of a given weight, then this is indicative that the foam layer 136 in mattress 100d has degraded and become too soft. In either case, if the mattress has become too hard or too soft, an alert message is provided, such as being communicated from circuitry 26 to one or more clinician notification devices 42 via network 38, to indicate that mattress 100d should be replaced.

The present disclosure contemplates that a standalone RADAR apparatus 12, 20, 22, 24 may be used with the patient support systems 10 disclosed herein, rather than been integrated into the particular patient support system such as at the time of manufacture. Thus, a standalone RADAR apparatus may retrofit onto an existing patient support system 10 such as a patient bed. The RADAR antennae 12 may be placed beneath the corresponding mattress and the other elements 20, 22, 24 may be packaged in a housing that attaches to the existing patient support system. Antennae 12 may be held in place with suitable fasteners (e.g., VELCRO® fasteners, straps, bands, screws, etc.) or adhesive or tape. Circuitry 24 may couple to an input port of circuitry 26 of the patient support system 10 for data exchange in some embodiments. Therefore, circuitry 24 may provide the standalone RADAR apparatus 12, 20, 22, 24 with plug-and-play capability by downloading software to circuitry 26 which circuitry 26 uses to control the respective pneumatic system 28 and/or actuators 32, for example, based on the data (e.g., TOF and/or distance data) received from circuitry 24.

A standalone RADAR apparatus 12, 20, 22, 24 also may be used for end-of-life testing of a mattress, particularly of a foam mattress like that shown in FIG. 11B. In such an embodiment, one or more RADAR antennae 12 is placed beneath the mattress 100d and one or more weights of known value may be placed atop the mattress 100d at one or more corresponding designated locations. If the mattress 100d has become too hard or too soft, as described above in connection with FIG. 11B, an alert message is provided, such as being displayed on a display screen provided with the housing carrying RADAR apparatus elements 20, 22, 24, for example.

The standalone RADAR apparatuses 12, 20, 22, 24 discussed above for retrofitting onto existing patient support systems or for use as mattress end-of-life testing, may be used with mattresses 100 of different types. Thus, in some embodiments, the housing of the standalone RADAR apparatus 10, 20, 22, 24 has one or more inputs that are used to select the type of mattress 100 with which the standalone RADAR apparatus 12, 20, 22, 24 is to be used. Based on the selected type of mattress, the appropriate TOF and/or distance thresholds are used in the various manners described elsewhere herein. In some embodiments in which circuitry 24 of the standalone RADAR apparatus communicates with circuitry 26 of the existing patient support system 10, inputs included in the patient support apparatus 10 and coupled to circuitry 26 are used to select the type of mattress being used.

Figure 12:
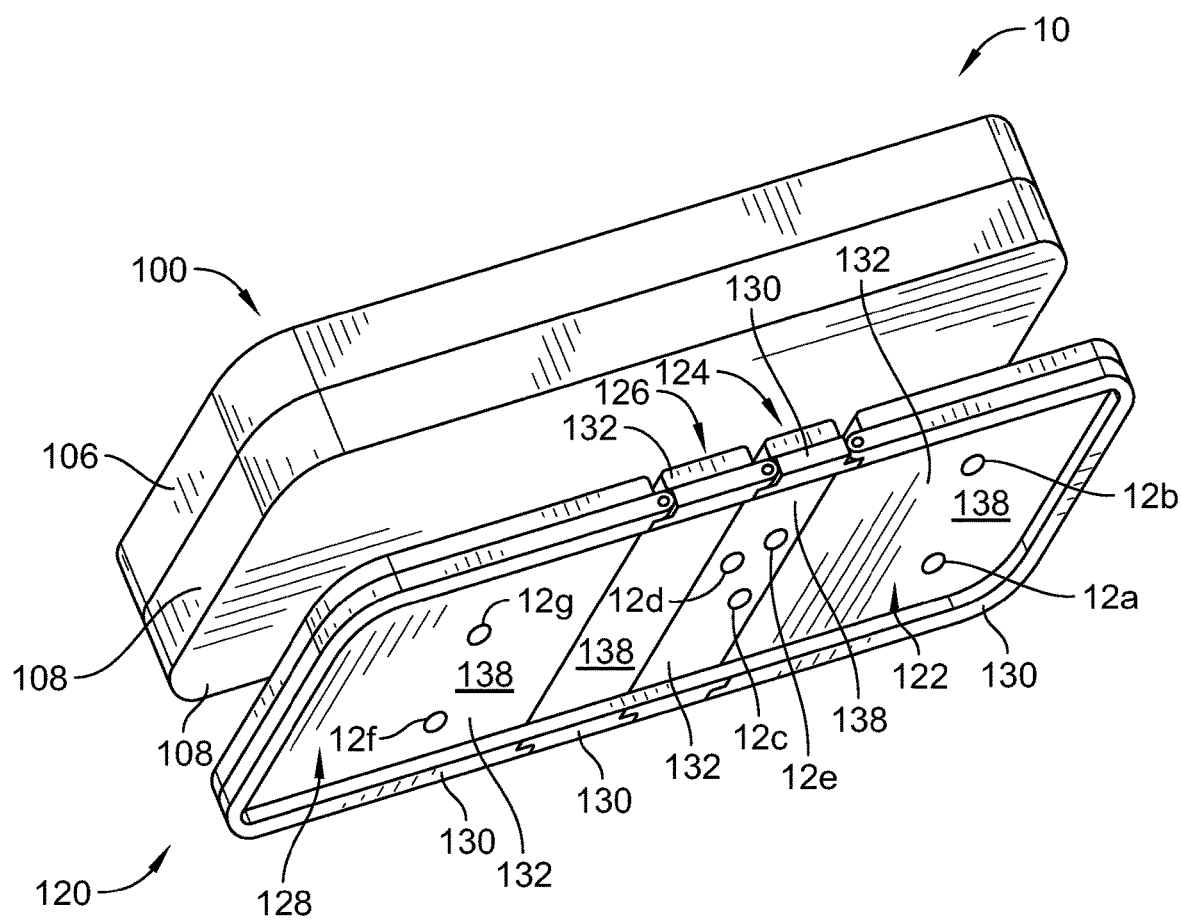
FIG. 12 is an exploded view of a portion of a patient support apparatus, similar to FIG. 11A, showing a mattress and an articulated mattress support deck of a frame of the patient support apparatus spaced downwardly from the mattress, a bottom surface of a head section of the mattress support deck having two RADAR antennae coupled thereto, a bottom surface of a seat section of the mattress support deck having three RADAR antennae coupled thereto, and a bottom surface of a foot section of the mattress support deck having two RADAR antennae coupled thereto.

Referring now to FIG. 12, an embodiment of patient support system 10 is depicted in which RADAR antenna 12a-g are coupled to a bottom surface 138 of panels 132 of head, seat, and foot sections 122, 124, 128 of mattress support deck 120. Except where noted below, the description above of the embodiment of FIG. 11a is equally applicable to the embodiment of FIG. 12, such as with regard to the placement of antennae 12a-g relative to the patient's bony prominences. Respective antennae feeds 52 for each antennae 12a-g are routed along bottom surface 138 to each corresponding antennae 12a-g. By placing antennae 12a-g on the bottom surface 138 of panels 138, some of the blind range of each antennae 12a-g is taken up by the thickness of the panels 132. This allows the upper boundary of the blind range of RADAR antennae 12a-g to be moved further downwardly within mattress 100 toward its bottom ticking layer 108 for a given pulse period as compared to the previously described embodiments in which antennae 12 are located inside of the respective mattress or on top surface 132 of panels 132 of deck 120. Alternatively, the period of pulse 14 can be made longer, if desired, and still have the upper boundary of the blind range at the same depth within mattress 100 as compared to the previously described embodiments.

As was the case with the embodiment of FIG. 11A, different types of mattresses can be placed on deck 120 of the embodiment of FIG. 12 and the impedance of impedance matching circuitry 22 adjusted accordingly. However, in the FIG. 12 arrangement having RADAR antennae 12a-g coupled to bottom surface 138 of panels 132 of deck 120, pulse 14 and the reflected signal 18 also travel through panels 132. Thus, the impedance of panels 132 contributes to the overall impedance of the environment to which impedance matching circuitry 22 is to be matched. Furthermore, TOF and distance, d, thresholds for determining the bottoming out condition, for example, are established within the software of circuitry 24 and/or circuitry 26 to account for the thickness of panels 132.

Figure 13:
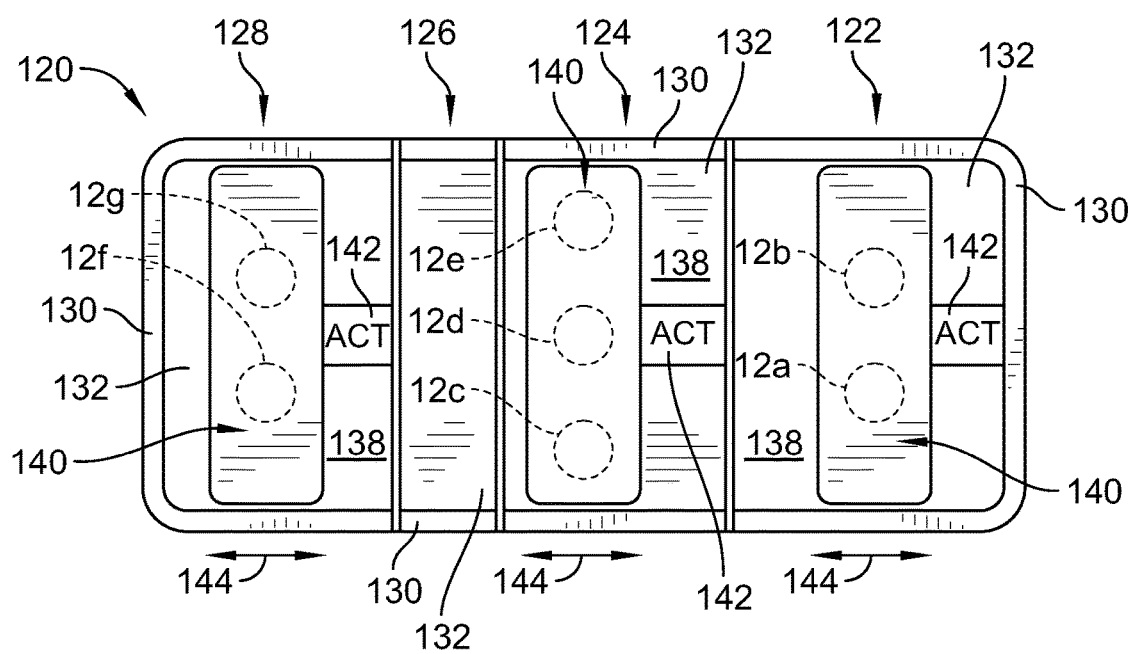
FIG. 13 is a bottom plan view of a mattress support deck, similar to the mattress support decks of FIGS. 11A and 12, showing the head, seat, and foot sections of the mattress support deck having movable plates coupled thereto, each movable plate carrying respective RADAR antennae and being movable along a longitudinal dimension of the mattress support deck to reposition the RADAR antennae in response to the operation of respective actuators (shown diagrammatically in FIG. 15)

Referring now to FIG. 13, a bottom plan view of mattress support deck 120 is shown. However, in the FIG. 13 embodiment, a movable antenna-support plate 140 is coupled to each of head, seat, and thigh sections 122, 124, 128 and respective RADAR antennae 12a-g are mounted to the respective plate 140. Specifically, RADAR antennae 12a, 12b are mounted to the plate 140 coupled to head section 122; RADAR antennae 12c, 12d, 12e are mounted to the plate 140 coupled to seat section 124; and RADAR antennae 12f, 12g are mounted to the plate 140 coupled to foot section 128. As shown diagrammatically in FIG. 13, an actuator 142 is provided on the bottom of each section 122, 124, 128 and is operable to move the respective plate 140, and therefore the RADAR antennae 12a-g supported by the respective plate 140, back and forth beneath sections 122, 124, 128 along the longitudinal dimension of deck 120 as indicated by double headed arrows 144.

Because different patients have different sizes and shapes, sometimes referred to as patient morphology, the ability to move RADAR antennae 12a-g relative to deck 120 and therefore, relative to the overlying mattress 100 and patient 16, allows RADAR antennae 12a-g to be positioned optimally beneath the patient where the patient's bony prominences immerse into the mattress 100 by the greatest amount. Furthermore, moving plates 140 from one end of each section 122, 124, 128 to the other end and taking TOF measurements and/or calculating distance, d, as the plates 140 move throughout their ranges of movement, allows an image to be made of the patient's immersion contour into the mattress 100 in some embodiments.

Circuitry 26 is coupled to each actuator 142 and controls the operation of each actuator 142 to move the respective plate 140 in some embodiments. It is worth noting that the RADAR antennae 12c-e on the plate 140 associated with seat section 124 are aligned in the lateral dimension of deck 120 rather than being arranged in the triangular pattern depicted in FIGS. 11A and 12. This is because during movement of plate 140 of seat section 124, RADAR antenna 12d will become positioned generally directly beneath the patient's coccyx at one position of plate 140 and RADAR antenna 12c, 12e will become positioned generally directly beneath the patient's right and left iliac tuberosity at another position of plate 140.

Figure 14:
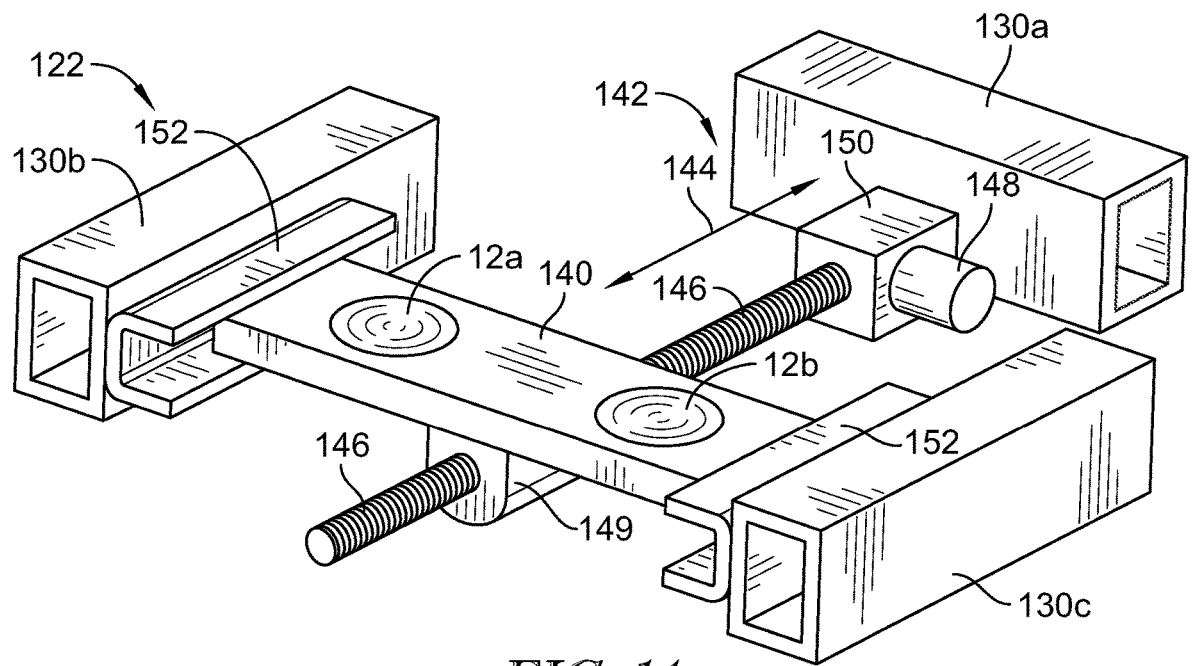
FIG. 14 is a perspective view of a portion of the mattress support deck of FIG. 15 showing C-shaped guides mounted to respective side frame members of the respective section of the mattress support deck, the guides receiving respective opposite ends of the movable plate therein, the actuator for moving the movable plate including a threaded jack screw extending through a threaded nut mounted to a bottom surface of the movable plate and a motor/gear reducer unit mounted to an end frame member and coupled to the jack screw, the motor/gear reducer unit being operable to rotate the jack screw to move the movable plate along the guides.
Figure 15:
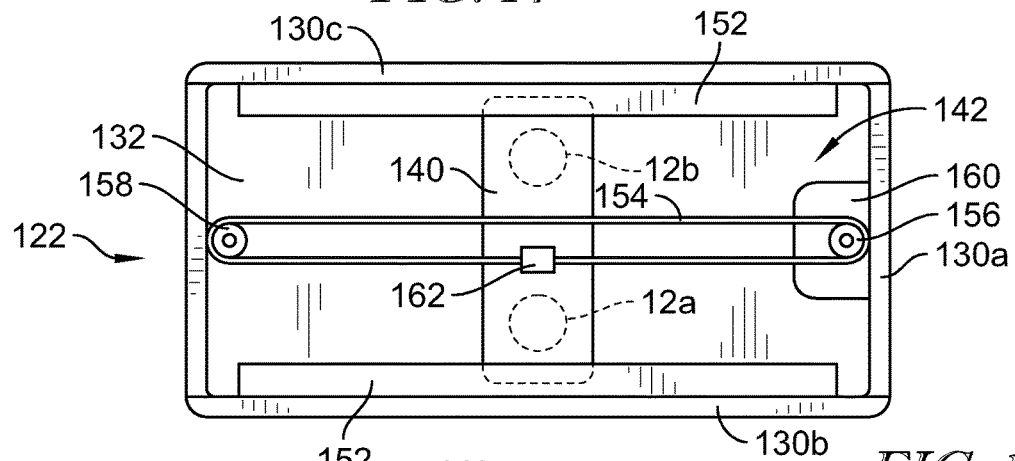
FIG. 15 is a bottom plan view of a deck section of the mattress support deck of FIG. 15 showing a first alternative actuator for moving the movable plate, the first alternative actuator including a flexible tether (e.g., cable, band, belt, or chain) trained around a motorized drive wheel (e.g., pulley or sprocket) and an idler wheel (e.g., pulley or sprocket), one flight of the flexible tether being anchored to the movable plate such that rotation of the motorized drive wheel by a corresponding motor moves the movable plate along the guides.

Referring now FIGS. 14-16, different examples of actuators 142 to move plates 140 relative to deck 120 are shown. These are given as illustrative examples and, therefore, it should be appreciated that other similar types of actuators may be used instead. In the description that follows with regard to FIGS. 14-16, actuators 142 as used on head section 122 of deck 120 are discussed. However, the discussion of actuators 142 as used on head section 122 is equally applicable to the use of actuators 142 on seat section 124 and foot section 128, and also on thigh section 126 for those embodiments having a movable plate 140 and one or more RADAR antennae 12 associated with thigh section 126.

As shown in the embodiment of FIG. 14, actuator 142 includes a threaded jack screw 146 and a motor 148 that operates through a gear reducer 150 to turn jack screw 146 in first and second directions depending upon whether plate 140 is to be moved toward a head end frame member 130a of framework 130 or away from head end frame member 130a. Motor 148 is coupled to circuitry 26 of patient support system 10 to receive command signals therefrom. A threaded nut 149 is coupled to the undersurface of plate 140 and extends downwardly therefrom. Jack screw 148 is threaded through nut 149. The threaded engagement between nut 149 and jack screw 148 results in nut 149 and plate 140 moving along jack screw 148 when jack screw is turned by the motor/gear reducer unit 148, 150. In the illustrative embodiment, gear box 150 is mounted to an inner side wall of frame member 130a. Suitable fasteners such as screws may be provided for this purpose. In other embodiments, gear box 150 and/or motor may be mounted to the overlying panel 132 either directly or via a bracket or the like hanging downwardly from the overlying panel 132.

In the illustrative FIG. 14 example, guides 152 having C-shaped cross sections are attached to inner walls of respective side frame members 130b, 130c of framework 130. End regions of plate 140 are received within the channels defined by the C-shaped guides 152. Thus, guides 152 support the respective plate 140 for sliding movement relative to head section 122 and constrain plate 140 to remain in its substantially parallel orientation with panel 132 of head section 122. Thus, the channels defined by the C-shaped guides 152 are sized so that ends regions of plate 140 fit within the channels with a minimal amount of clearance therebetween. In alternative embodiments, guides 152 are omitted and frame members 130b, 13c are configured with integral guides. For example, in some embodiments, the inner walls of frame members 130b, 130c may have slots therethrough that are sized for receipt of end regions of plate 140 therein. In other embodiments, the inner walls of frame members 130b, 130c themselves may be formed with grooves to define C-shaped channels therein.

As is suggested in FIG. 14, the upper surface of plate 140 that carries RADAR antennae 12a, 12b is spaced vertically downwardly by a slight distance such as on the order of about % inch to about 1 inch from the bottom surface of the overlying panel 132. Thus, an air gap between RADAR antennae 12a, 12b and panel 132 exists in the FIG. 13-16 embodiments in which plates 140 are provided on deck 120. The air gap contributes to the overall impedance of the environment to which impedance matching circuitry 22 is to be matched. It is known that free space, such as that of the air gap, has an impedance of 377Ω. This disclosure contemplates that RADAR antenna 12 may be supported up to 10 cm or more below the upper surface 134 of deck 120.

Also, by placing antennae 12a, 12b on plate 140 with an air gap between plate 140 and panel 132, some of the blind range of each antenna 12a, 12b is taken up by the air gap as well as the thickness of the panels 132. This allows the upper boundary of the blind range of RADAR antenna 12a, 12 be to be moved even further downwardly within mattress 100 toward its bottom ticking layer 108 for a given pulse period as compared to the previously described embodiment of FIG. 12 in which antennae 12 are located on the undersurface of panels 132 of deck 120. Alternatively with regard to the FIG. 13-16 embodiments, the period of pulse 14 can be made longer, if desired, and still have the upper boundary of the blind range at the same depth within mattress 100 as compared to the previously described embodiments.

As shown in the embodiment of FIG. 15, actuator 142 includes a flexible tether 154 (e.g., cable, band, belt, or chain) trained around a motorized drive wheel 156 (e.g., pulley or sprocket) and an idler wheel 158 (e.g., pulley or sprocket). A motor 160 is mounted to frame member 130a and/or panel 132 and is operated under the control of circuitry 26 of rotate drive wheel 156 in first and second opposite directions depending upon whether plate 140 is to be moved toward frame member 130a or away from frame member 130a in the longitudinal dimension of head section 122. An anchor 162 is provided to affix one flight of the flexible tether 154 to plate 140 such that rotation of the motorized drive wheel 156 by motor 160 moves the movable plate along the guides 152. The axes about which drive wheel 156 and idler wheel 158 rotate is generally perpendicular to panel 132 and plate 140. The discussion above regarding alternative guides, impedance matching, and blind range boundary location in connection with the FIG. 14 embodiment is equally applicable to the FIG. 15 embodiment.

As shown in the embodiment of FIG. 16, actuator 142 includes a multi-stage scissors linkage 164 interconnected between end frame member 130a of head section 122 and movable plate 140. A motor 166 is mounted to the end frame member 130a and/or panel 132 and is operable to pivot a main link 168 of the scissors linkage 164 in first and second opposite directions, as indicated by double headed arrow 170, to extend and retract the scissors linkage 164 to move the movable plate 140 along the guides 152 relative to panel 132. A first slider 172 is provided at the head end of linkage 164 and a second slider 174 is provided at the foot end of linkage 164. Slider 172 slides along a bail 176 and slider 174 slides along plate 140 as scissors linkage 164 extends and retracts. The discussion above regarding alternative guides, impedance matching, and blind range boundary location in connection with the FIG. 14 embodiment is equally applicable to the FIG. 16 embodiment.

According to this disclosure, antennae 12 are tuned by impedance matching circuitry 22 to match the environment through which pulse 14 and reflected signal 18 travel to the driver circuitry 20, which in some embodiments is typically about 50Ω to about 70Ω. In particular, antennae 12 are tuned to the environment of patient support system 10. In the disclosed embodiments, antennae 12 are not radiating entirely into free space, but rather into a mattress and/or into a frame of patient support system 10. Thus, in some embodiments, the antennae 12 are tuned to match the impedance of the mattress for the case of the in-mattress antennae 12. In other embodiments, the antennae 12 are tuned to match the impedance of the frame and mattress of patient support system 10 for the case of the below-mattress antennae 12.

As mentioned above, some embodiments of the antennae 12 disclosed herein exhibit the characteristic of circular polarization. However, it is within the scope of this disclosure for antennae 12 to be configured to exhibit the characteristic of horizontal, vertical, or elliptical polarization at the option of the designer.

In some embodiments, patient support system 10 may have an array of antennae 12, all connected to one RADAR system 12, 20, 22, 24, and optionally, the RADAR system may multiplex between the antennae 12 of the antenna array. Alternatively, the patient support system 10 may use an array of RADAR systems 12, 20, 22, 24, each with one or more antenna 12. In some embodiments, the system 10 may use a bi-static RADAR system 12, 20, 22 24.

In addition to the blind range issue that causes RADAR system 12, 20, 22, 24 to not be able to see very close objects, RADAR system 12, 20, 22, 24 also must deal with removing clutter from the reflected signal 18. Clutter is created by objects that provide RADAR returns that are irrelevant. For example, return signals reflecting off of internal components of the mattress or components of the frame of patient support apparatus 10. In other words, return signals reflected by anything other than the target or object 16 of interest is considered to be unwanted clutter. Accordingly, circuitry 24 and/or circuitry 26 is programmed or configured to reduce the effects of clutter.

On way to reduce clutter is to use background subtraction to ignore the portions of the mattress and/or frame of patient support system 10 that are not of interest. For example, RADAR system 12, 20, 22, 24 may be operated to emit one or more pulses 14 and take a measurement of the one or more reflected signals 18 when no patient 16 is present on the patient support apparatus 10. The one or more reflected signals 18 under these conditions represent a background signal which, in many instances, will be reflections from components that are different ranges than the patient 16 will be. Circuitry 24 or circuitry 26 is programmed to subtract the "no patient" reflected signal data from the reflected signal data when the patient 16 is on the mattress.

In some embodiments, circuitry 24 or circuitry 26 may be configured to implement a pulse compression algorithm. By using pulse compression, the TOF or distance, d, to the target 16 can be determined even though the pulse is longer (i.e., pulse length (distance)=pulse length in seconds×speed of light) than the distance between RADAR antennae 12 and the object 16. For example, pulse compression is one possible way of distinguishing between the RADAR pulse reflection 18 from the mattress and the RADAR pulse reflection 18 from the patient 16. These reflections will likely be so close together that the pulse length (in distance) is larger than the antenna-to-patient distance, d. Pulse compression may be accomplished by frequency analysis such as by using linear modulation, non-linear modulation, or a coded waveform such as a Costas code and also by phase modulation. It should be noted that use of pulse compression will adversely effect the detection range of the RADAR apparatus 12, 20, 22, 24 and so is only suitable for those embodiments in which RADAR antennae 12 are located at a sufficient distance from the patient 16 that the bottoming out condition or related thresholds are still detectable or determinable despite the adverse effects.

Inherently, there is noise in the RADAR system 12, 20, 22, 24. Thus, each RADAR ranging sample provides an estimate of the distance, d, to the patient 16 from the respective antenna 12. Assuming there is random noise, averaging the signals (e.g., TOF or distance, d) together provides a better estimate of the actual distance, d, to the patient 16 than a single ranging measurement. The averaging may be done by circuitry 24 or circuitry 26 on the raw radar signal (average raw radar data, then use the averaged data to produce a range estimate) or on the range estimates (each radar ranging sample is used to create a range estimate, then many range estimates are averaged). The averaging may be done in multiple steps, for example on the raw signal and subsequently on the range estimates. In some embodiments, oversampling (sample at a rate higher than the Nyquist rate) is implemented by circuitry 24 or circuitry 26 so that the signal observations are strongly correlated.

In some embodiments, circuitry 24 or circuitry 26 is programmed to implement pulse-pair processing to determine what targets 16 (e.g., which portions of the patient 16) are moving by comparing the phase of successive pulse pairs (i.e., the phase of successive reflected signals 18). If there is an object 16 at a certain range that has no change in phase in successive reflected signals 18, it is considered clutter by circuitry 24 or circuitry 26 and ignored. On the other hand, a patient 16 who is breathing and has blood-mass movement due to the patient's heartbeat will have a several degree phase shift at GHz frequencies between successive reflected signals 18. Thus, if the phase of the received signals 18 are always the same, then the object from which the signals 18 are reflected isn't moving and so the associated signals 18 are ignored.

In some embodiments, circuitry 24 or circuitry 26 is programmed to implement a Doppler filter. That is, the reflected signals 18 are processed to determine the magnitude of a Doppler shift and one or more filters (e.g., software filters) are used to determine what data to include and what data to exclude from further analysis or processing. Only targets 16 producing a Doppler shift in the region or interest are considered. For example, if reflected signals 18 having a Doppler shift of less than a first frequency, F1, and more than a second frequency, F2, are kept, then a band-pass filter is implemented. If reflected signals 18 having a Doppler shift less than a first frequency, F1, are kept, a low pass filter is implemented. Such a filter may be used to keep the non-moving clutter for further use (e.g., background subtraction) or future analysis, if desire. If reflected signals 18 having a Doppler shift more than a second frequency, F2, then a high pass filter is implemented.

In some embodiments, the at least one RADAR apparatus 12, 20, 22, 24 and/or control circuitry 26 of patient support apparatus 10 is configured to determine a heart rate (HR) and/or a respiration rate (RR) of the patient. For example, the Doppler shift information just described may be processed to determine the HR and the RR. Alternatively or additionally, the circuitry 24 or circuitry 26 may implement a ballistocardiography algorithm to determine the HR and the RR. For example, a first Doppler filter may be implemented by circuitry 24 or circuitry 26 to detect chest movement due to a heartbeat of the patient to determine the HR. Similarly, a second Doppler filter may be implemented by circuitry 24 or circuitry 26 to detect diaphragm movement of the patient to determine the RR. Thus, circuitry 24 or circuitry 26 uses the Doppler shift information from signals 18 to determine the HR and the RR.

In some embodiments, RADAR antennae 12 are configured as an array of RADAR antennae 12 as mentioned above. The array of RADAR antennae 12 may include a phased-grid array of antennae 12, for example. A phased-grid array of antennae 12 permits beam steering or beam forming of the emitted pulses 14 so that the pulses 14 are aimed at various portions of the target 16 that are not necessarily directly vertically above the emitting antennae 12, or stated more accurately, so that the emitted pulse 14 wave is at an angle other than 90 degrees to the plane defined by the one or more emitting antennae 12. The beam steering/forming may be accomplished, for example, by adjusting the phase of the emitted pulses 14 of adjacent antenna 12 of the phased-grid array so that the pulses 14 are either more in phase or more out of phase so as to shape the overall emitted pulse 14 beam. Changing the phase of the pulses 14 of adjacent antennae 12 changes the direction and/or shape of the beam defined by the emitted pulses 14. Because beam forming is based on phase differences, it works with narrow band signals. Furthermore, use of beam forming may improve the ranging accuracy by up to 1 cm at close range, such as in the patient support system 10 embodiments disclosed herein. Beam forming may also be accomplished by changing a distance between RADAR antennae 12 according to this disclosure.

Optionally, one or more RADAR lenses may be used with respective RADAR antennae 12 to improve the ranging accuracy. A RADAR lens focuses the emitted pulse 14 wave to a more localized area of the target. It should be noted that use of one or more RADAR lenses may be more appropriate for the embodiments in which RADAR antennae 12 are outside of the mattress, and particularly, in the embodiments of FIGS. 12-16 in which RADAR antennae are beneath mattress support deck 120. This is because the thickness of the one or more RADAR lenses may possibly be felt by the patient 16 if placed inside of a mattress. Known RADAR lenses include, for example, the Luneburg lens and the Maxwell's fish-eye lens. In some embodiment, RADAR antennae 12 may be carried by a respective housing that also carries the RADAR lens. Thus, each RADAR antenna, housing, and lens may be packaged together as a unit. A port for coupling of the antenna feed 52, such as a coaxial cable, may be provided on an external surface of the housing. Alternatively, the antenna feed 52 may include a short segment of cable that extends from the housing and that terminates at an electrical connector.

As noted above, the RADAR systems contemplated herein are capable of determining a patient's heart rate and/or respiration rate. Thus, the present disclosure contemplates embodiments in which patient support apparatus 10 includes patient support frame 110, patient support surface 100 supported on the patient support frame 110, and a RADAR system 12, 20, 21, 22, 24 carried by the patient support frame 110. The RADAR system 12, 20, 21, 22, 24 is operable to determine a depth to which a patient is immersed into the patient support surface 100 and is also operable to perform a Doppler analysis to determine at least one of a heart rate or a respiration rate of the patient. In some embodiments, the RADAR system 12, 20, 21, 22, 24 is operable to determine both the heart rate and respiration rate of the patient.

The RADAR system 12, 20, 21, 22, 24 includes electronically steerable RADAR sensors, such as electronically steerable RADAR antennae, in some embodiments. For example, the electronically steerable RADAR sensors include a plurality of transmitting antennae 12a and a plurality of receiving antennae 12b. The plurality of transmitting antennae 12a and the plurality of receiving antennae 12b are arranged in a grid beneath an upper surface of the patient support surface 100.

In some embodiments, signals 18 received by the plurality of receiving antennae 12b are used by the RADAR system 12, 20, 21, 22, 24 for body contour mapping. The body contour mapping may, in turn, be used by circuitry 24, circuitry 26, and/or remote server 40, or some other computer device, to make one or more of a variety of subsequent determinations such as one or more of the following: determining whether the patient is at risk of developing pressure ulcers; determining a Braden score for the patient including determining a patient mobility sub-factor of the Braden score; determining functional decline of the patient; determining a location on the patient support surface of at least one of the patient's legs, arms, trunk, pelvis or head; determining whether the patient is side-lying, lying on their stomach, or lying on their back; determining whether the patient has slid toward a foot end of the patient support surface or whether the patient is in a proper position on the patient support surface 100 of the patient support apparatus 10; determining sleep quality of the patient; or determining impending exit of the patient from the patient support apparatus 10.

In connection with determining the patient mobility sub-factor of the Braden score, the following numerical values are given: 1. Completely Immobile—the patient does not make even slight changes in body or extremity position without assistance; 2. Very Limited—the patient makes occasional slight changes in body or extremity position but is unable to make frequent or significant changes independently; 3. Slightly Limited—the patient makes frequent though slight changes in body or extremity position independently; and 5. No Limitations—the patient makes major and frequent changes in position without assistance.

In some embodiments, inflation of at least one air bladder 30 of one or more air bladders 30 of the patient support surface 100 is adjusted based on whether the patient is side-lying, lying on their stomach, or lying on their back as determined from the body contour mapping. Alternatively or additionally, inflation of at least one air bladder 30 of one or more air bladders 30 of the patient support surface 100 is adjusted based on whether the patient has slid toward the foot end of the patient support surface 100 as determined from the body contour mapping. When it is stated herein that "inflation" of an air bladder is "adjusted," both inflation of the air bladder (i.e., increasing pressure by adding air) and deflation of the air bladder (i.e., decreasing pressure by removing air) are covered by such language.

In some embodiments, the RADAR system 12, 20, 21, 22, 24 is operable to determine a distance, d, to the patient 16 or to a surface 112 of the patient support surface 100 adjacent the patient 16 for each receiving antenna 12b of the plurality of receiving antennae 12b by using (i) a time-of-flight (TOF) between transmission of pulses 14 from the plurality of transmitting antennae 12a and receipt by the plurality of receiving antennae 12b of the reflected signal 18 that is reflected back from the patient 16 or reflected back from the surface 112 of the patient support surface 100 adjacent the patient, (ii) antenna beam angle and geometry, and (iii) signal strength.

The present disclosure contemplates that the Doppler analysis to determine at least one of a heart rate or a respiration rate of the patient includes a micro-Doppler analysis that determines a phase change between first signals 14 that are transmitted by the plurality of transmitting antennae 12a and second signals 18 that are received by the plurality of receiving antennae 12b. The Doppler analysis is used to determine one or more of the following: detection of a heart beat; premature ventricular contractions (PVC's) of the patient's heart; rate-based arrhythmias of the patient's heart; lethal arrhythmias of the patient's heart; onset of congestive heart failure; or progression of congestive heart failure. Alternatively or additionally, the Doppler analysis is used to detect apnea, including obstructive sleep apnea, of the patient.

Figure 18:
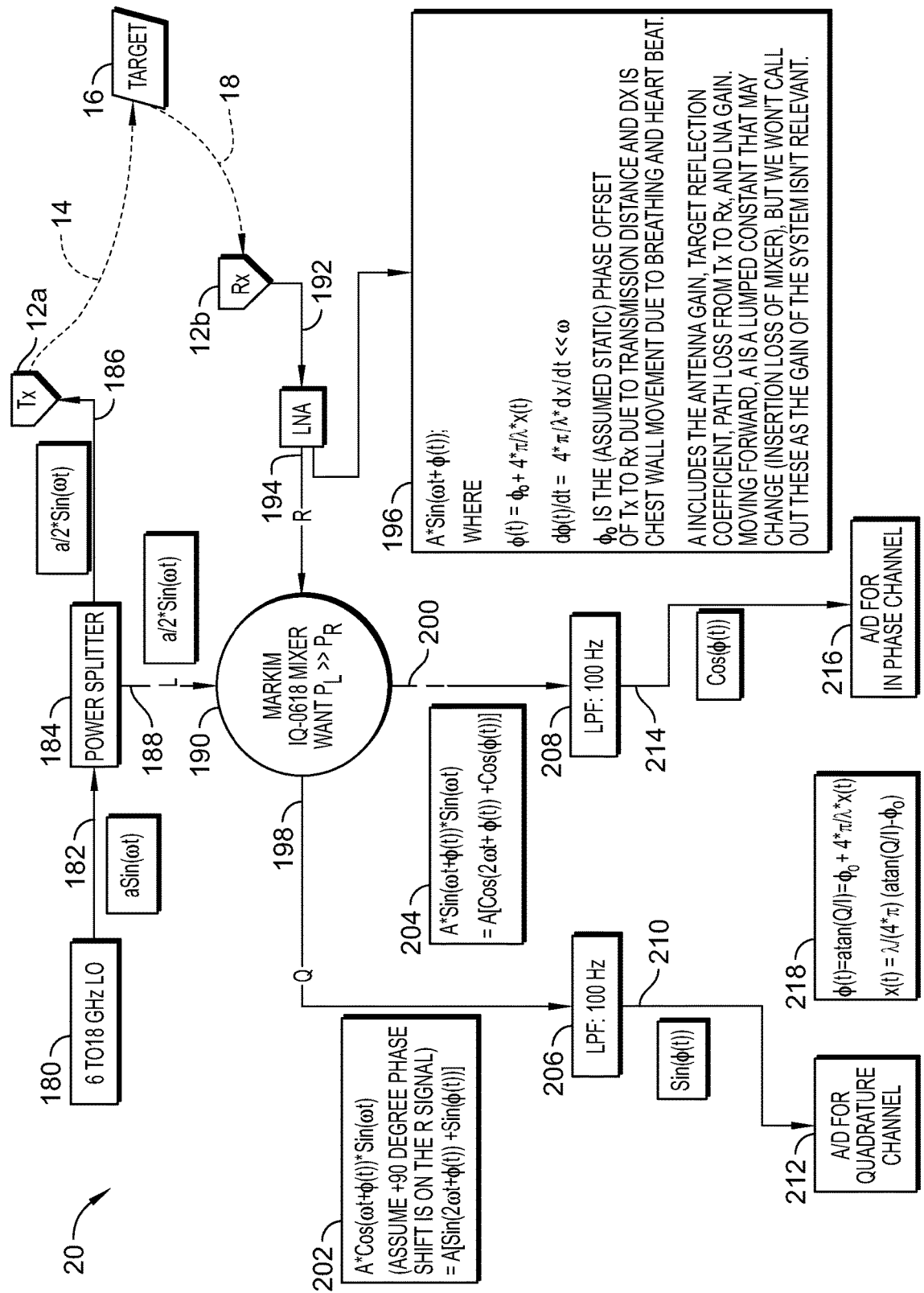
FIG. 18 is a block diagram of a RADAR apparatus or system showing the RADAR system including a local oscillator, a power splitter having an input coupled to the local oscillator, at least one transmitting antenna coupled to a first output of the power splitter, a mixer having a first input coupled to a second output of the power splitter, at least one receiving antenna coupled to a second input of the mixer, a first low pass filter having an input coupled to a quadrature output of the mixer, a second low pass filter having an input coupled to an in-phase output of the mixer, a first analog-to-digital converter coupled to an output of the first low pass filter, and a second analog-to-digital converter coupled to an output of the second low pass filter.

Referring now to FIG. 18, one example of the RF driver/receiver circuitry 20 of one embodiment of a RADAR system for detecting a patient's heart beat and/or respiration includes a local oscillator (LO) 180 which produces an output signal 182 that is communicated to an input of a power splitter 184. In the illustrative example, signal 182 is output by LO 180 in the form a $Sin(\omega t)$ with a frequency of about 6 GigaHertz (GHz) to about 18 GHz. Power splitter 184 has a first output from which a first output signal 186 is communicated to transmitting antenna 12a and power splitter 184 has a second output from which a second output signal 188 is communicated to a local oscillator input (L) of a mixer 190. In the illustrative example, signals 186, 188 are each of the form $a/2 \times Sin(\omega t)$. Thus, power splitter 190 splits signal 182 in half.

The transmitting antenna 12a of FIG. 18 emits pulse 14 which is reflected by the target 16 as signal 18 which is, in turn, received by the receiving antenna 12b in a similar manner as described above in connection with other embodiments. An output signal 192 from the receiving antenna 12b is input into a low-noise amplifier (LNA) 192 and an output signal 194 from the LNA 192 is communicated to a reflected signal input (R) of mixer 190. As indicated in block 196 of FIG. 18, signal 194 output from LNA 192 is of the form $A \times Sin(\omega t + \phi t)$ where $\phi(t) = \phi_o + 4\pi/\lambda \times x(t)$ and $d\phi(t)/dt = 4\pi/\lambda \times dx/dt << \omega$. In the foregoing formulae, $\phi_o$ is the (assumed static) phase offset of transmitting antenna 12a to receiving antenna 12b due to transmission distance and dx is chest wall movement due to breathing and heartbeat. The coefficient, A, includes the gain of antennae 12a, 12b, target reflection coefficient, path loss from transmitting antenna 12a to receiving antenna 12b, and LNA gain. The A coefficient is a lumped constant that may change (e.g., due to insertion loss of mixer 190), but gain of the RADAR system is not relevant in connection with determining the phase change due to Doppler shifting.

In the illustrative example, mixer 190 is a model no. IQ-0618 mixer available from Marki Microwave, Inc. of Morgan Hill, California. As noted above the L input of mixer 190 receives signal 188 from power splitter 188 and the R input of mixer 190 receives signal 194 from LNA 192. As indicated by the text "Want $P_L >> P_R$" in mixer block 190, it is desirable that the power level of signal 188 at the L input of mixer 190 be much greater than the power level of signal 194 at the R input of mixer 190, such as on the order of ten times greater for example. Mixer 190 produces a quadrature signal 198 at a Q output of the mixer 190 and an in-phase signal 200 at an I output of the mixer 190.

As indicated in block 204 of FIG. 18, the in-phase signal 200 is of the form $A \times Sin(\omega t + \phi(t)) \times Sin(\omega t)$ which is equal to $A \times [Cos(2\omega t + \phi(t)) + Cos(\phi(t))]$. As indicated in block 202 of FIG. 18, the quadrature signal 198 is of the form $A \times Cos(\omega t + \phi(t)) \times Sin(\omega t)$ which is equal to $A \times [Sin(2\omega t + \phi(t)) + Sin(\phi(t))]$ due to the +90 degree phase shift on the Q signal 198 as compared to the I signal 200. A first low pass filter (LPF) 206 of the RADAR system of FIG. 18 has an input that receives the quadrature signal 198 from the Q output of the mixer 190 and a second low pass filter (LPF) 208 of the RADAR system of FIG. 18 has an input that receives the in-phase signal 200 from the I output of mixer 190. In the illustrative example, each LPF has a cutoff frequency that is set to about 100 Hz but LPF's having cutoff frequencies in the range of about 2,000 kilohertz (kHz) to about 10 Hz are also believed to be suitable.

An output signal 210 from the first LPF 206 is input into a first analog-to-digital (A/D) converter 212 for the quadrature channel and an output signal 214 from the second LPF 208 is input into a second A/D converter 216 for the in-phase channel. The output signal 210 is of the form $Sin((t))$ and the output signal 214 is of the form $Cos(\phi(t))$. Thus, the LPF's 206, 208 filter out the $2\omega t + \phi(t)$ component of respective quadrature and in-phase signals 198, 200. As indicated at block 218 of FIG. 18, the digital Q and I outputs of respective A/D converters 212, 216 are processed, such as by circuitry 24 in some embodiments, to determine $\phi(t)$ and $x(t)$ by using the formulae $\phi(t) = a\, tan(Q/I) = \phi_o + 4\pi/\lambda \times x(t)$ and $x(t) = \lambda/(4\pi) \times (a\, tan(Q/I) - \phi_o)$.

It is recognized by those familiar in the art that the features of the block diagram may be implemented using elements on a printed circuit board, for example a Microsemi MDU1020 series planar transceiver, which is an X-band motion detector that utilizes Doppler shift phenomenon to sense motion. As a specific example, for narrow band RADARs, a 90-degree phase shift may be implemented with a length of transmission line that is one-quarter wavelength long. Similarly, the features indicated in FIG. 18 may be implemented as a system on chip, for example an AWR1642 single-chip RADAR sensor manufactured by Texas Instruments.

By taking distance measurements, x(t), over time, a displacement graph is generated for one or more locations on a grid at which the steerable radar sensors (e.g., antenna 12a. 12b) are aimed or focused. To produce the patient's heart beat signal and to determine the patient's heart rate and respiration rate, averaging and filtering algorithms are implemented for selected displacement measurements, x(t), such as those in which one or more radar sensors are aimed at the patient's upper thorax region. Furthermore, the x(t) measurements for all locations on the grid can be used to generate a body contour map. The grid may be established by X and Y coordinates on a reference plane which, if desired, can correspond to an upper surface of the mattress 100 in which case displacement x(t) is measured downwardly from the reference plane at each grid point due to immersion of the patient into the mattress 100. Alternatively, the reference plane may correspond to the upper surfaces of antennae 12a. 12b that are located within or beneath the mattress 100 in which case distance, d, upwardly from the reference plane to the object 16 is adjusted at each X-Y grid location based on the x(t) measurements. It should be appreciated that distance measurements, x(t), appearing in FIG. 18 and referenced above, correspond to movement in the Z direction (e.g., generally vertical) if the X-Y reference plane is established as a generally horizontal plane.

Figure 19:
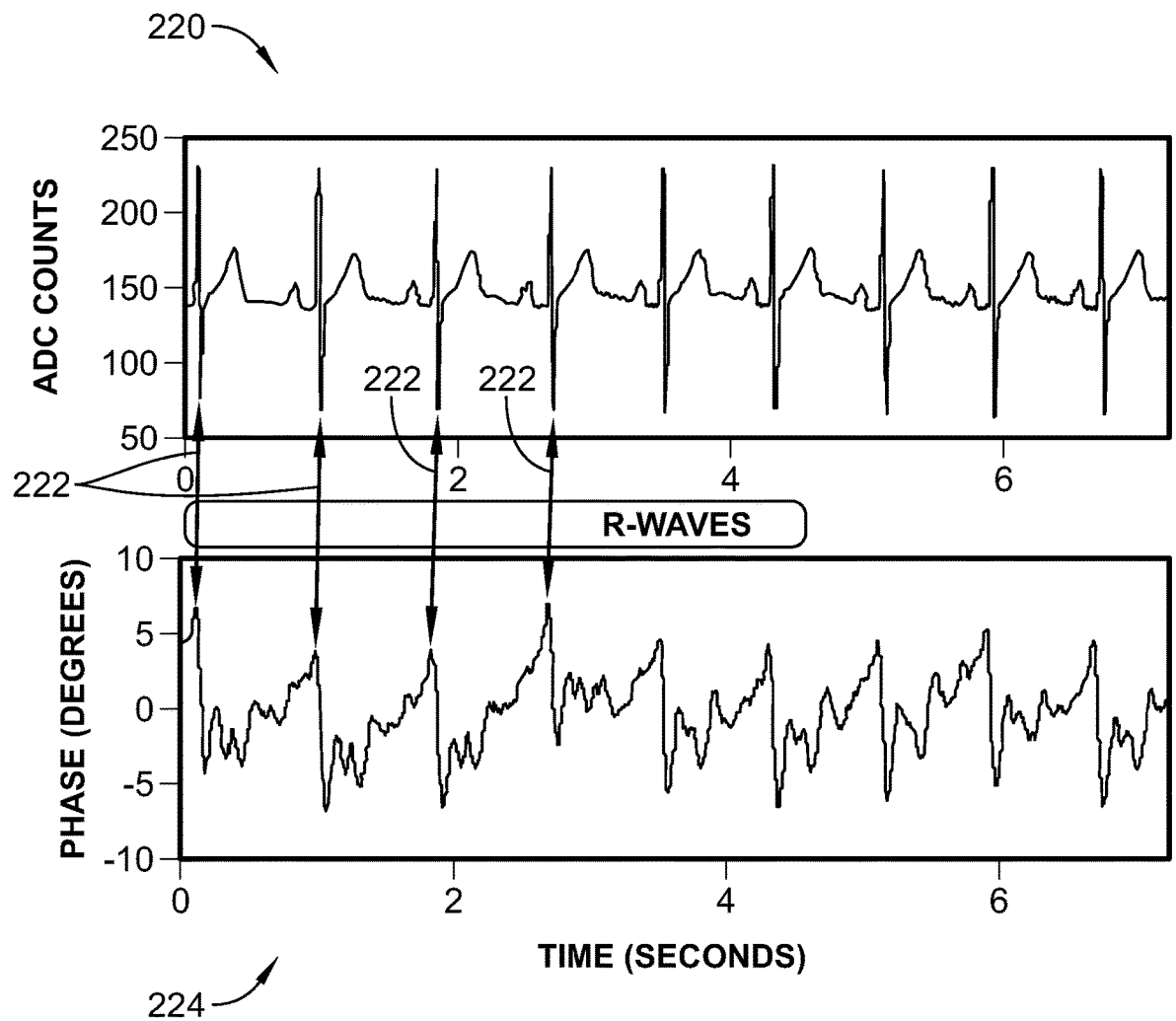
FIG. 19 includes a pair of graphs showing an electrocardiograph signal in an upper graph and a phase graph in the lower graph with R-wave arrows indicating correspondence between R-wave spikes in the upper and lower graphs to indicate that the phase measured by the RADAR apparatus of FIG. 18 is usable to determine heart rate of a patient.

Referring now to FIG. 19, an upper graph 220 shows an example of a trace or graph from an electrocardiograph (EKG) with the x-axis of graph 220 being time in seconds and the y-axis being analog to digital converter (ADC) counts. The ADC counts is a normalized value representing a measured voltage of the electrical activity of a beating heart. A lower graph 224 of FIG. 19 is the phase, $\phi(t)$, as determined by the system 20 of FIG. 18. Graph 224 is generated, in some embodiments, based on measurements from a single radar sensor (e.g., single antenna pair 12a, 12b) being aimed at a patient's chest continuously or at least for an extended period of time. In lower graph 224, the x-axis is time in seconds and corresponds to the x-axis of upper graph 220 and the y-axis is phase in degrees. A series of double headed arrows 222 in FIG. 19 show that R-wave spikes in the upper graph 220 coincide with phase spikes of the lower graph. Thus, the spikes corresponding to the R-waves in the measured phase, $\phi(t)$, can be used to calculate the patient's heart rate.

Although certain illustrative embodiments have been described in detail above, variations and modifications exist within the scope and spirit of this disclosure as described and as defined in the following claims.

The invention claimed is:

1. A patient support apparatus comprising
a patient support frame,
a patient support surface supported on the patient support frame, and
a RADAR system carried by the patient support frame and operable to determine a depth to which a patient is immersed into the mattress and to perform a Doppler analysis to determine at least one of a heart rate or a respiration rate of the patient, wherein the RADAR system comprises a local oscillator, a power splitter having an input coupled to the local oscillator, at least one transmitting antenna coupled to a first output of the power splitter, a mixer having a first input coupled to a second output of the power splitter, at least one receiving antenna coupled to a second input of the mixer, a first low pass filter having an input coupled to a quadrature output of the mixer, a second low pass filter having an input coupled to an in-phase output of the mixer, a first analog-to-digital converter coupled to an output of the first low pass filter, and a second analog-to-digital converter coupled to an output of the second low pass filter.

2. The patient support apparatus of claim 1, wherein the RADAR system is operable to determine both the heart rate and respiration rate of the patient.

3. The patient support apparatus of claim 1, wherein the RADAR system comprises electronically steerable RADAR sensors.

4. The patient support apparatus of claim 3, wherein the electronically steerable RADAR sensors comprise a plurality of transmitting antennae and a plurality of receiving antennae.

5. The patient support apparatus of claim 4, wherein the plurality of transmitting antennae and the plurality of receiving antennae are arranged in a grid beneath an upper surface of the patient support surface.

6. The patient support apparatus of claim 4, wherein signals received by the plurality of receiving antennae are used by the RADAR system for body contour mapping.

7. The patient support apparatus of claim 6, wherein the body contour mapping is also used to determine whether the patient is at risk of developing pressure ulcers.

8. The patient support apparatus of claim 6, wherein the body contour mapping is used in connection with determining a Braden score for the patient including determining a patient mobility sub-factor of the Braden score.

9. The patient support apparatus of claim 6, wherein the body contour mapping is used in connection with determining functional decline of the patient.

10. The patient support apparatus of claim 6, wherein the body contour mapping is used to determine a location on the patient support surface of at least one of the patient's legs, arms, trunk, pelvis, or head.

11. The patient support apparatus of claim 6, wherein the body contour mapping is used to determine whether the patient is side-lying, lying on their stomach, or lying on their back.

12. The patient support apparatus of claim 11, wherein the patient support surface includes one or more air bladders and inflation of at least one air bladder of the one or more air bladders is adjusted based on whether the patient is side-lying, lying on their stomach, or lying on their back.

13. The patient support apparatus of claim 6, wherein the body contour mapping is used to determine whether the patient has slid toward a foot end of the patient support surface or whether the patient is in a proper position on the patient support apparatus.

14. The patient support apparatus of claim 13, wherein the patient support surface includes one or more air bladders and inflation of at least one air bladder of the one or more air bladders is adjusted based on whether the patient has slid toward the foot end of the patient support surface.

15. The patient support apparatus of claim 6, wherein the body contour mapping is used to determine sleep quality of the patient.

16. The patient support apparatus of claim 6, wherein the body contour mapping is used to determine impending exit of the patient from the patient support apparatus.

17. The patient support apparatus of claim 1, wherein the RADAR system includes a plurality of transmitting antennae and a plurality of receiving antennae and wherein the RADAR system is operable to determine a distance to the patient or to an upper layer of the patient support surface for each receiving antenna of the plurality of receiving antennae by using (i) the TOF between transmission of pulses from each of the plurality of transmitting antennae and receipt by each of the plurality of receiving antennae of a reflected signal that is reflected back from the patient or reflected back from the upper layer, (ii) antenna beam angle and geometry, and (iii) signal strength.

18. The patient support apparatus of claim 17, wherein the Doppler analysis to determine at least one of a heart rate or a respiration rate of the patient comprises a micro-Doppler analysis that determines a phase change between first signals transmitted by the plurality of transmitting antennae and second signals received by the plurality of receiving antennae.

19. The patient support apparatus of claim 1, wherein the Doppler analysis is used to determine one or more of the following: premature ventricular contractions (PVC's) of the patient's heart; rate-based arrhythmias of the patient's heart; lethal arrhythmias of the patient's heart; onset of congestive heart failure; or progression of congestive heart failure.

20. The patient support apparatus of claim 1, wherein the Doppler analysis is used to detect sleep apnea of the patient.

21. The patient support apparatus comprising of claim 1, wherein
the patient support surface further comprises a core including at least one patient support element and a ticking having an upper layer overlying the core, and
wherein the RADAR system includes at least one RADAR antenna situated beneath the core, the at least one RADAR antenna emitting a pulse that travels through the core and that is reflected by either the patient or the upper layer of the ticking as a reflected signal back to the at least one RADAR antenna, and processor circuitry that determines a time-of-flight (TOF) of the pulse and the reflected signal to determine whether the patient supported on the patient support surface is at risk of contraction of pressure ulcers due to improper immersion into the patient support surface.

22. The patient support apparatus of claim 1, wherein the RADAR system is instantiated as a system-on-chip.

* * * * *

UNITED STATES PATENT AND TRADEMARK OFFICE
CERTIFICATE OF CORRECTION

PATENT NO. : 11,938,072 B2
APPLICATION NO. : 17/578713
DATED : March 26, 2024
INVENTOR(S) : Frank E. Sauser et al.

It is certified that error appears in the above-identified patent and that said Letters Patent is hereby corrected as shown below:

In the Claims

Column 42, Line 58, Claim 21, delete the phrase "comprising of" and insert the word --of--.

Signed and Sealed this
Seventh Day of May, 2024

Katherine Kelly Vidal
*Director of the United States Patent and Trademark Office*